(12) United States Patent
Lee

(10) Patent No.: US 9,186,457 B2
(45) Date of Patent: Nov. 17, 2015

(54) INTRAVENOUS INFUSION MONITORING APPARATUS, SYSTEM AND METHOD

(76) Inventor: Freddie Eng Hwee Lee, Singapore (SG)

( * ) Notice: Subject to any disclaimer, the term of this patent is extended or adjusted under 35 U.S.C. 154(b) by 206 days.

(21) Appl. No.: 14/114,076

(22) PCT Filed: Apr. 10, 2012

(86) PCT No.: PCT/SG2012/000125
§ 371 (c)(1),
(2), (4) Date: Dec. 11, 2013

(87) PCT Pub. No.: WO2012/148356
PCT Pub. Date: Nov. 1, 2012

(65) Prior Publication Data
US 2014/0155867 A1   Jun. 5, 2014
US 2015/0073392 A2   Mar. 12, 2015

Related U.S. Application Data

(60) Provisional application No. 61/479,629, filed on Apr. 27, 2011.

(51) Int. Cl.
| | |
|---|---|
| A61M 5/00 | (2006.01) |
| G01F 1/708 | (2006.01) |
| A61M 5/168 | (2006.01) |
| G01F 1/684 | (2006.01) |
| G01F 15/00 | (2006.01) |

(52) U.S. Cl.
CPC ........... *A61M 5/16886* (2013.01); *G01F 1/684* (2013.01); *G01F 1/6847* (2013.01); *G01F 15/001* (2013.01); *A61M 5/16804* (2013.01); *A61M 5/16831* (2013.01)

(58) Field of Classification Search
None
See application file for complete search history.

(56) References Cited

U.S. PATENT DOCUMENTS

| 4,384,578 A | 5/1983 | Winkler |
| 4,813,280 A | 3/1989 | Miller et al. |
| 4,938,079 A | 7/1990 | Goldberg |

(Continued)

FOREIGN PATENT DOCUMENTS

| DE | 44 04 395 A1 | 8/1995 |
| JP | 01009187 A | 1/1989 |
| JP | 01037382 A | 2/1989 |
| WO | WO 2009/144726 A1 | 12/2009 |

OTHER PUBLICATIONS

International Search Report from International Application No. PCT/SG2012/000125 mailed Jul. 23, 2012.

(Continued)

*Primary Examiner* — Harshad R Patel
(74) *Attorney, Agent, or Firm* — Wolf, Greenfield & Sacks, P.C.

(57) ABSTRACT

An intravenous infusion system that shows infusion flow rate, volume of medication infused, and alarming during malfunction. User intervention to adjust flow rates deviation is possible, using the data already stored in the system prior to the onset of making the adjustment. The system detects flow rate by measuring temperature dynamics in a section of the fluid path, unlike other systems that measures the electromechanical output of the pumping source if the counting of drops is not possible. This fundamental difference allows the invention to be used in any system that has a pumping source that provides a continuous fluid path as it measures actual flow of fluid in a segment of the fluid path, independent of pumping mechanism design.

22 Claims, 20 Drawing Sheets

(56) References Cited

U.S. PATENT DOCUMENTS

| | | |
|---|---|---|
| 5,891,096 A | 4/1999 | Hyun et al. |
| 6,083,206 A * | 7/2000 | Molko .......................... 604/253 |
| 6,367,666 B1 | 4/2002 | Hou et al. |
| 6,948,636 B1 | 9/2005 | Fischer et al. |
| 7,337,922 B2 | 3/2008 | Rake et al. |
| 7,914,500 B2 | 3/2011 | Gafner-Geiser et al. |
| 2004/0026448 A1 | 2/2004 | Pichotte et al. |
| 2014/0048558 A1 | 2/2014 | Lee |

OTHER PUBLICATIONS

Written Opinion for International Application No. PCT/SG2012/000125.

International Search Report and Written Opinion from International Application No. PCT/SG2012/000146 mailed Jul. 30, 2012.

* cited by examiner

INTRAVENOUS INFUSION MONITORING APPARATUS, SYSTEM AND METHOD

TECHNICAL FIELD

Embodiments of the invention relate to a system, apparatus, and methods for monitoring intravenous (IV) infusion, in particularly the flow rate and volume of infusion delivery to a patient.

BACKGROUND

In infusion therapy, the patient could either be immobilized at bed site or ambulatory. In the former, infusion consist of an intravenous (IV) drip set with gravity means or with the aid of an electronic IV pump while in the latter the patient is ambulatory with a self powered pump like elastomeric or electronic pumps. The inadequacies in either situations relate to the lack of the flow rate display of a gravity IV drip set as well as flow rate drifts of such, hence necessitating frequent drip rate checks and roller clamp adjustments by a healthcare provider. In electronic pumps the flow rate display relates to the functioning of the driving mechanism of such pumps and not the monitoring of actual flow of medication to the patient.

Therefore, improved infusion procedures that address these inadequacies are desirable. In conventional mechanical infusion apparatus like elastomeric, spring powered or gas powered pumps, flow adjustments are non-existent while in electrically driven pumps user/healthcare provider response relates to malfunctioning of the pumping mechanism itself.

It is the object of this invention to provide monitoring of IV infusion by measuring the actual flow of medication independent of the driving mechanism of the source and using the techniques disclosed to enhance patient safety and caregiver efficacy.

SUMMARY

According to one embodiment of the invention, a thermal pulse (or heat pulse) is emitted into the fluid or medication whose flow rate is determined by measuring the time taken for this thermal pulse and any change in its level to be detected by a thermal sensor (e.g. temperature sensor) located at a fixed position downstream in relation to the flow direction. This time duration and change in temperature and the fixed distance between the emitting and sensing locations provide the inputs to determine flow velocity. The volumetric flow rate of the fluid is then derived from the product of the flow velocity (V) and the cross-sectional area (A) for flow. Even when different types of fluids with different thermal coefficient are used, the impact arising from such variables has little or no influence as the measurement involves taking time duration between successive pulses. While flow rate is determined by time and temperature measurements, occlusion is detected by comparing the temperature detected by two temperature sensors located at one upstream location and another downstream location in relation to the fluid delivery channel or path. In the absence of occlusion, the temperature at the two locations will be different, specifically the temperature at the downstream site will be higher than the temperature at the upstream site due to the thermal pulse emitted between the two locations. The fluid absorbs thermal energy from the pulse and flows downstream, resulting in a higher temperature detected at the downstream location. On the other hand, the presence of occlusion causes minimal or no flow which results in a minimal temperature difference or substantially equal temperature readings at the two sensor locations.

According to one embodiment of the invention, the section of the fluid delivery channel or path that is used in the above described measurements of flow rate and temperature difference is enclosed within an in-line Flow Cell, which can be inserted or attached to a control module (Flow Detection Unit) that measures and displays the appropriate flow status. The Flow Detection Unit comprises a thermal source that utilizes a Laser diode, infra-red (IR) diode or any heat generating means. The thermal source emits the thermal pulse(s) that transfers heat to the fluid in the channel of the Flow. Cell. The temperature sensors in the Flow Detection Unit measure the temperatures at the predetermined locations in the Flow Cell and provide these as input data for further processing by the microprocessor in the Flow Detection Unit. The algorithm programmed in the microprocessor will convert these temperature inputs into digital outcomes and display instantaneous flow rate, mean flow rate and/or volume delivered.

According to another embodiment of the invention, the Flow Cell comprises a bar code that can be read as it is swiped along a slot in the housing of the Flow Detection Unit. The bar code is encoded to provide specific input data for the microprocessor or MCU in the Flow Detection Unit, which obviates the need for manual input by the user of such data, hence promoting plug and play simplicity. The barcode, which can be preprinted on the Flow Cell, can also contain unique identification such that when the Flow Cell is swiped in the Flow Detection Unit, the patient data tagged to the barcode is scanned/read by the Flow Detection Unit, which displays patient data for nurse verification. This provides for positive identification of patient to the IV pump, i.e. medication prescribed to the patient. Barcode can also be tagged with a desired flow rate of the medication for the patient. In the situation where patient and medication data are managed in a server with wireless connectivity, such information could be sent to the Flow Detection Unit by remote means. This allows further means of verifying that correct medication is administered to the patient as the Flow Detection Unit is attached to the Flow Cell through which medication flows.

BRIEF DESCRIPTION OF THE DRAWINGS

Embodiments of the invention will be readily understood by the following detailed description in conjunction with the accompanying drawings.

DETAILED DESCRIPTION

Figure 1:
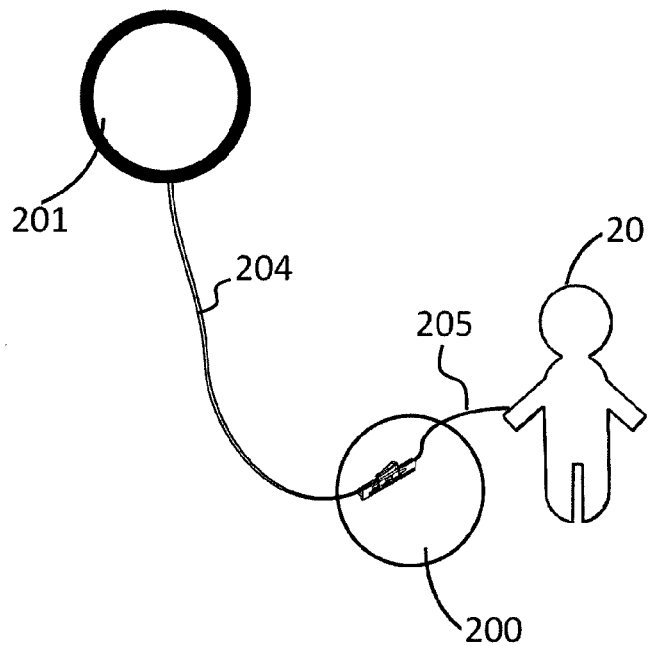
FIG. 1 is a schematic view of the intravenous (IV) infusion monitoring system in accordance with one embodiment of the invention.

In the following description, numerous specific details are set forth in order to provide a thorough understanding of various illustrative embodiments of the invention. It will be understood, however, to one skilled in the art, that embodiments of the invention may be practiced without some or all of these specific details. In other instances, well known intravenous delivery processes and mechanisms have not been described in detail in order not to necessarily obscure pertinent aspects of embodiments being described.

Embodiments of the invention relate to an infusion monitoring and measurement system that supports mobile or ambulatory and bed side mode of infusion based on any mechanical or electrical source of pumping fluid source. In an embodiment of the invention, a control module (Flow Detection Unit), which is a tablet or pod like device, displays data and alarms to provide effective monitoring of a typical infusion procedure and allows appropriate user response. In another embodiment, a flow section of the fluid path (Flow Cell) is attachable to the Flow Detection Unit to enable measurement and monitoring of the fluid flow, volume of fluid delivered and other related parameters.

The Flow Detection Unit comprises at least one thermal or heat source such as a laser diode or Infra Red (IR) diode or any heat generating means, at least one thermal sensing means, and electronic processing circuits to ascertain flow rates and occlusion, and in certain application modes prompts the user or healthcare provider to take specific actions in order to achieve desired flow of medication or fluids to the patient. In one embodiment, the Flow Cell is an in-line component of the fluid delivery path between the fluid source and the patient. The Flow Cell allows thermal energy/thermal signal emitted from the Flow Detection Unit to be transferred to the fluid or medication that flows through the flow cell. In one embodiment, certain portions of the Flow Cell include heat transmission paths, e.g. contacts or conductive probes, which facilitate the heating or temperature measurement of the fluid or medication by the Flow Detection Unit. The Flow Cell may function as an interface on the fluid delivery path which allows specific measurement of the fluid (by the Flow Detection Unit) while it is delivered to the patient, hence making it amenable as a single use or disposable component that could be easily assembled with the entire fluid delivery apparatus. In one embodiment, the Flow Cell is bar-coded to allow automatic input of relevant data related to the fluid delivery apparatus used, for example flow rate and volume to be infused or even unique patient or pump or medication related identification.

One advantage of the re-usable main body Flow Detection Unit and a single use in-line installed Flow Cell allows all current disposable mechanical pumps including and not limited to spring powered, gas powered or elastomeric pumps to be equipped with a safety feature indicating flow rates and occlusion that is not available presently. The implication is significant as the use of such pumps, which is well received for its ease of use could be expanded to include infusion of medication with narrow therapeutic tolerances. Without such means to show the flow status, and where appropriate prompting user intervention the use of such medication with such pumps would be limited, and even hazardous. Furthermore, unlike monitoring systems in most electronic pumps that focuses on the proper functioning of the pump itself, the Flow Cell and Flow Detection Unit monitors the actual flow rate of infusion and in some embodiments allow the necessary adjustment to the flow orifice to achieve the desired flow.

For example, the Flow Detection Unit provides a display of flow rates, such as instantaneous and mean rate of infusion, and the volume delivered as means of alerting the healthcare provider to undesirable deviations. It may also alert the healthcare provider when occlusion is detected. The Flow Detection also allows user/healthcare provider to make adjustments to correct the flow rates as a means of addressing the risks associated with any non-action.

In addition, the Flow Detection Unit supports positive identification of patient/drug patency. Conventionally, drugs to be infused are prepared in the pharmacy while the filled apparatus are attached to patients by a separate healthcare provider. Patient and intended medication data stored in the Flow Detection Unit by means of a barcode wand or hand held scanner in the pharmacy can be subsequently used as positive identification means when the infusion monitoring is initiated. For example, the nurse will be able to identify the correct matching of medication in the pump to the patient when the Flow Detection Unit displays patient data that is tagged to the barcode on the Flow Cell. This helps to reduce incorrect infusion of medication to the patient. Barcode could also be tagged with a desired or nominal flow rate data for the medication to be administered to the patient. As an interface between the Flow Detection Unit and the fluid delivery path, the Flow Cell is not necessarily an integral part of the delivery system. It could be configured as an in-line component of an extension tube that could be connected to any infusion delivery system to support monitoring of infusion described in this invention.

Figure 2:
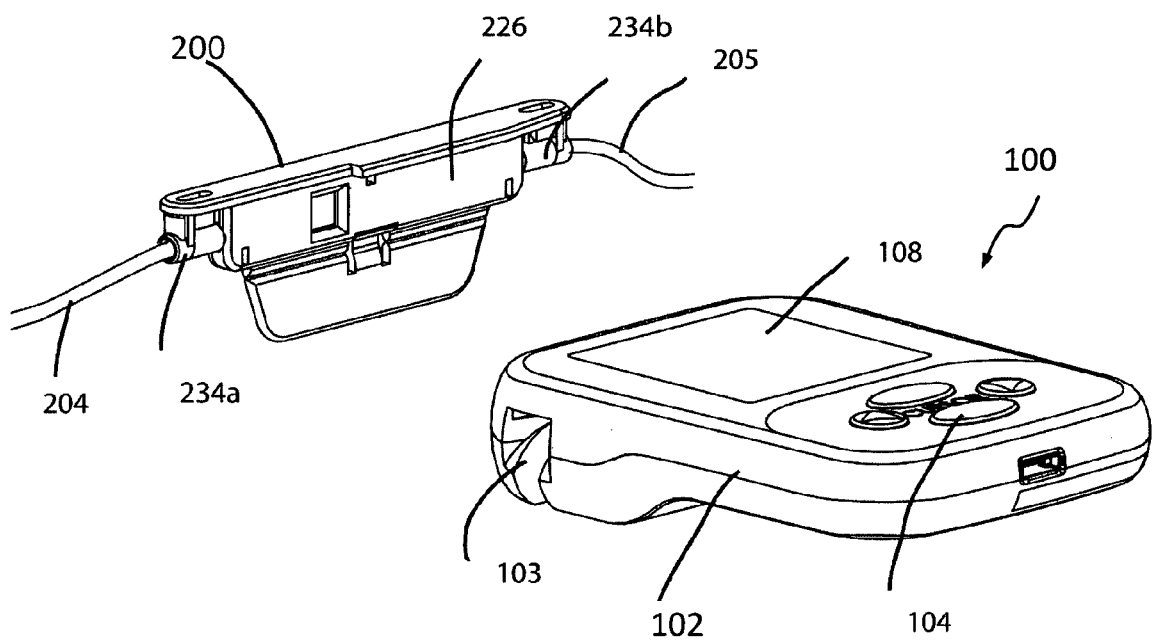
FIG. 2 is a perspective view of the Flow Detection Unit and Flow Cell in accordance with one embodiment of the invention.

Referring to FIG. 1 and FIG. 2, a Flow Cell 200 according to one embodiment of the present invention forms a segment of a fluid path of a fluid delivery system, e.g. an intravenous infusion system, from a fluid source 201 to a final receiving point, e.g. a patient 20. The fluid source 201 can be an electrical fluid pump or a mechanical fluid pump (e.g. spring powered, gas powered or elastomeric fluid pumps). In one embodiment, the Flow Cell 200 includes a first plate 246 and a second plate 247 connected to each other. In the context of a patient receiving medication, the Flow Cell 200, when inserted into an opening or slot 103 in the Flow Detection Unit 100, enables the flow rate of infusion to be detected and shown on a display screen 108 of Flow Detection Unit 100. The display screen 108 could be a Liquid Crystal Display (LCD) or Organic Light-Emitting Diode (OLED) display with or without in-screen navigational options for displaying flow rates, flow rate deviations, volume delivered and visual alarms for occlusions or unacceptable deviations in flow rates, etc. The Flow Detection Unit 100 can also include an audio alarm that activates when unsafe flow rates or occlusion are detected.

The Flow Detection Unit 100 with the Flow Cell 200 may be dimensioned to be attachable to the patient 20 so that it allows easy access to the caregiver, e.g., a physician or nurse, to adjust the rate of infusion when needed, to reset an alarm button 104 or merely to monitor the flow status on display screen 108. In one embodiment, the Flow Detection Unit 100 starts automatically when Flow Cell 200 is inserted or secured thereto, an in-built proximity switch will initiate the MCU in the Flow Detection Unit 100 to perform the preprogrammed logic.

Figure 2A:
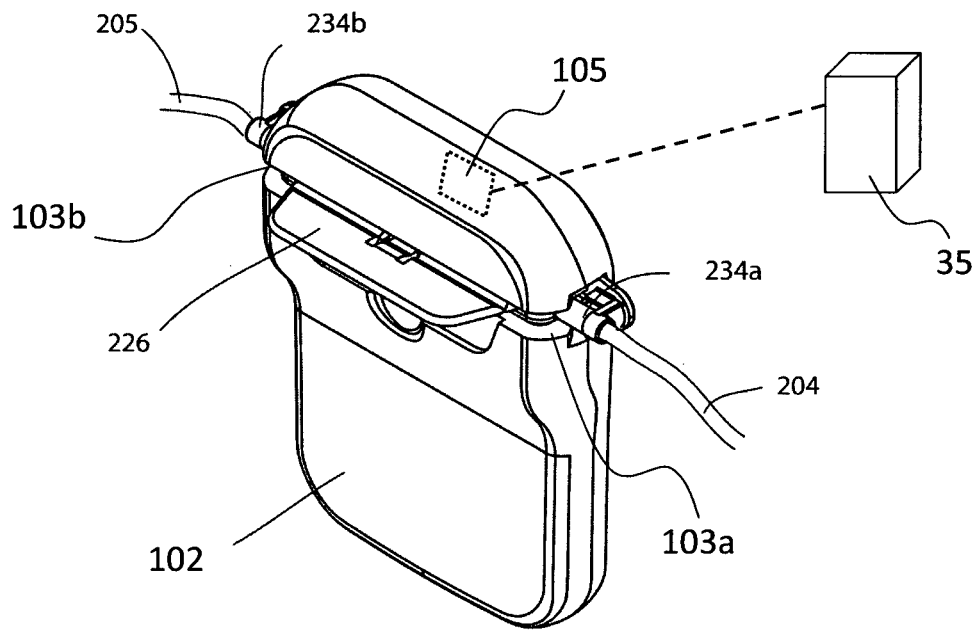
FIG. 2A is a perspective view of the Flow Detection Unit with Flow Cell attached in accordance to one embodiment of the invention.
Figure 2B:
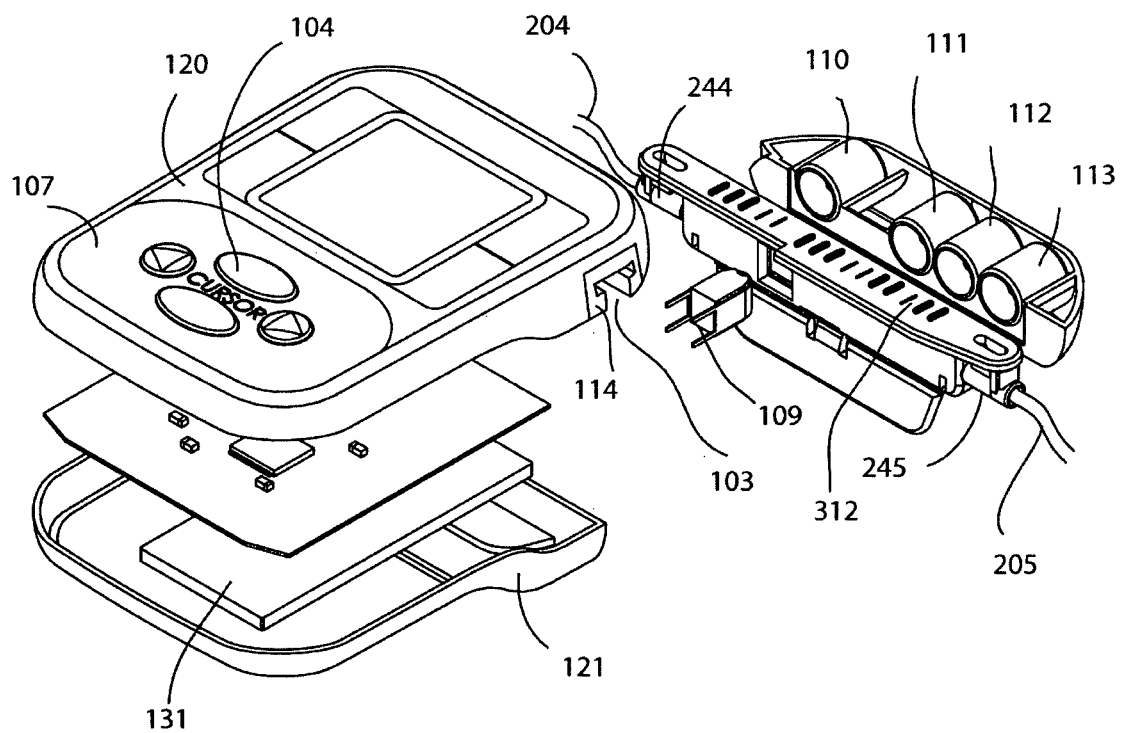
FIG. 2B is an unassembled perspective view of the Flow Detection Unit with its associated components in accordance with the one embodiment of the invention.
Figure 2C:
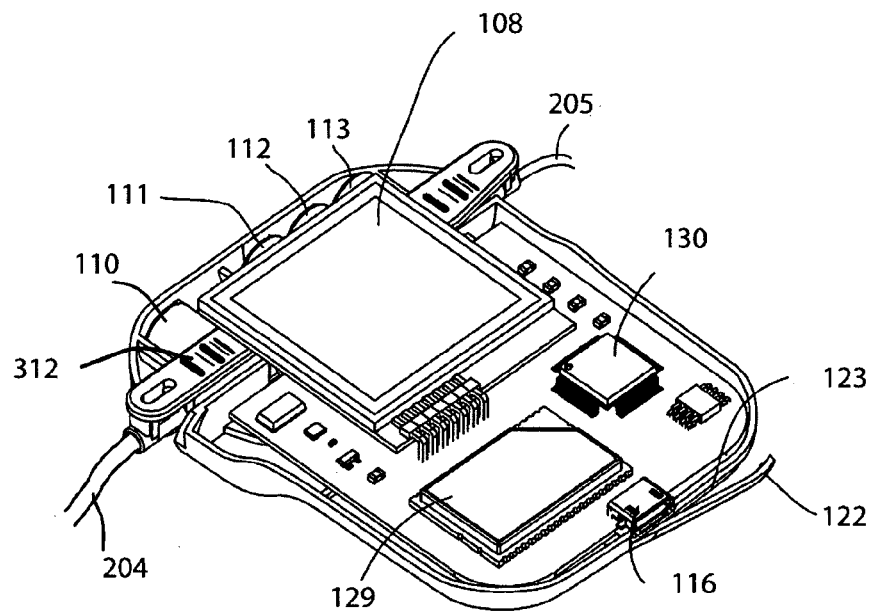
FIG. 2C is a perspective view of the Flow Detection Unit in use with the flow cell in accordance with one embodiment of the invention.

Referring to FIG. 2B and FIG. 2C, the Flow Detection Unit 100 comprises a thermal source 109 and first, second, third and fourth thermal sensors 110, 111, 112 and 113. The use of more thermal sensors enables time and amplitude data to be recorded at more positions along the fluid channel. This in turn increases the permutations in the development of the algorithm for flow rate detection. The thermal source 109 is a flexible resistive heater, but it could be any source generating thermal energy, e.g. a laser diode, an IR diode or the like. In one embodiment, the thermal source 109 is positioned in substantially equidistant between the first and second thermal sensors 110 and 111. However, it is also possible that the distances from thermal source 109 to thermal sensors 110 and 111 are not substantially equidistant. If this is the case, an algorithm used to determine the measurement/monitoring results could be developed to compensate for the impact of such non-equidistance positioning relationship between thermal source 109 and first and second thermal sensors 110 and 111, in the data recorded. The thermal sensors 110, 111, 112 and 113 are radiation or temperature sensing means that uses, for example IR sensors, laser sensors, film based resistance temperature detectors (RTD) sensors, negative/positive temperature coefficient (NTC/PTC) thermistors or any thermocouple.

Figure 3A:
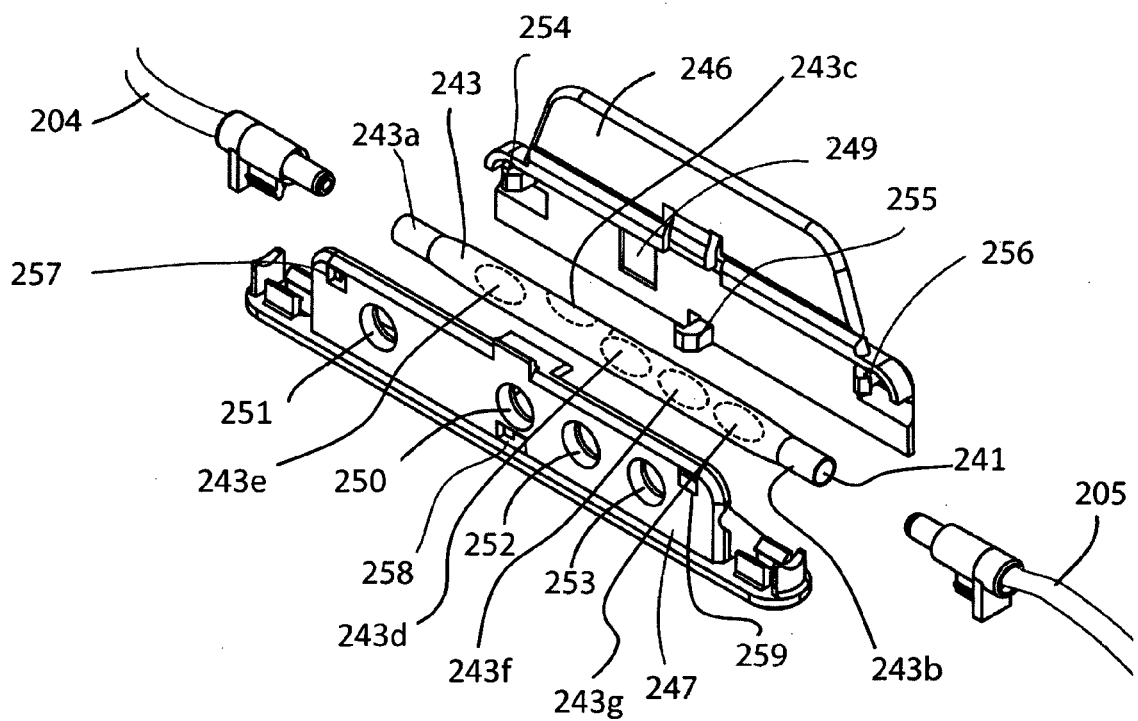
FIG. 3A and FIG. 3B are perspective views of the Flow Cell in accordance with one embodiment of the invention.
Figure 3B:
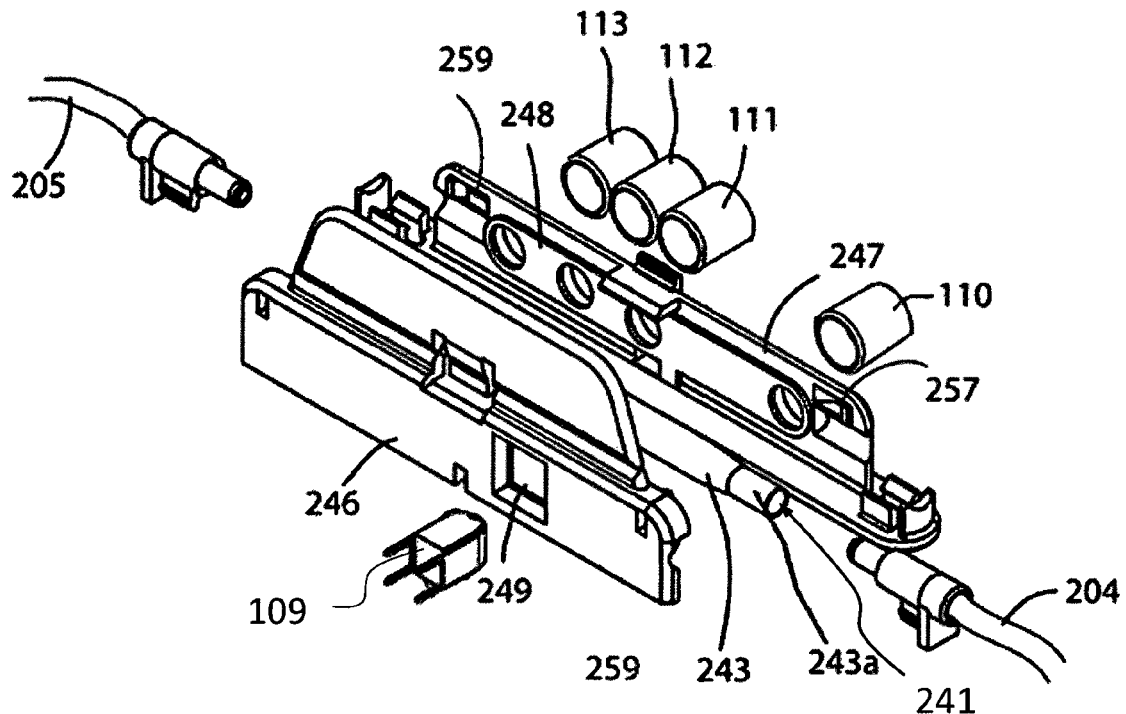
Figure 3C:
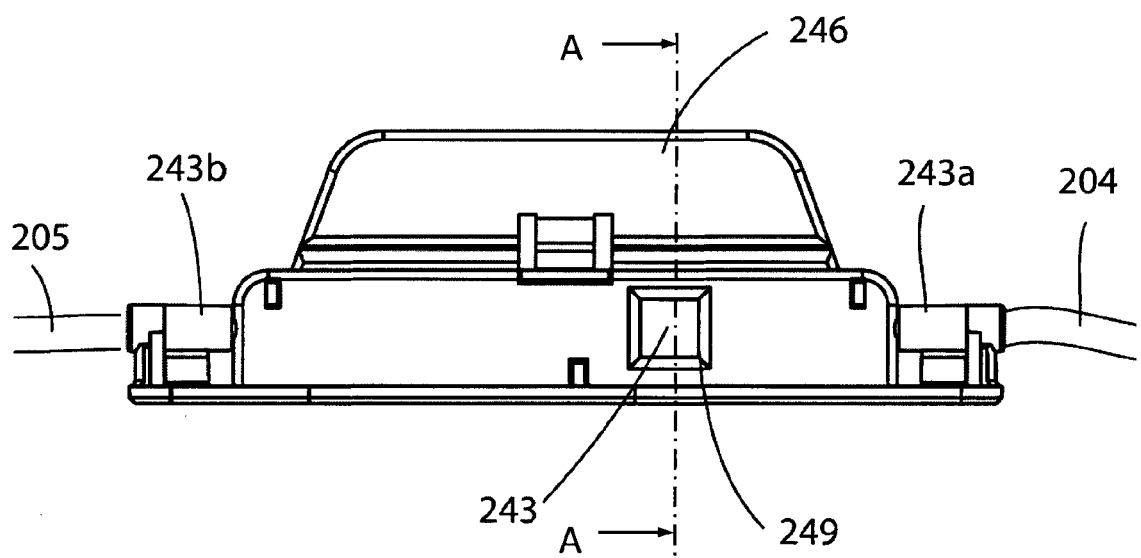
FIG. 3C and FIG. 3D are side views of the Flow Cell illustrated in FIG. 3A and FIG. 3B.
Figure 3D:
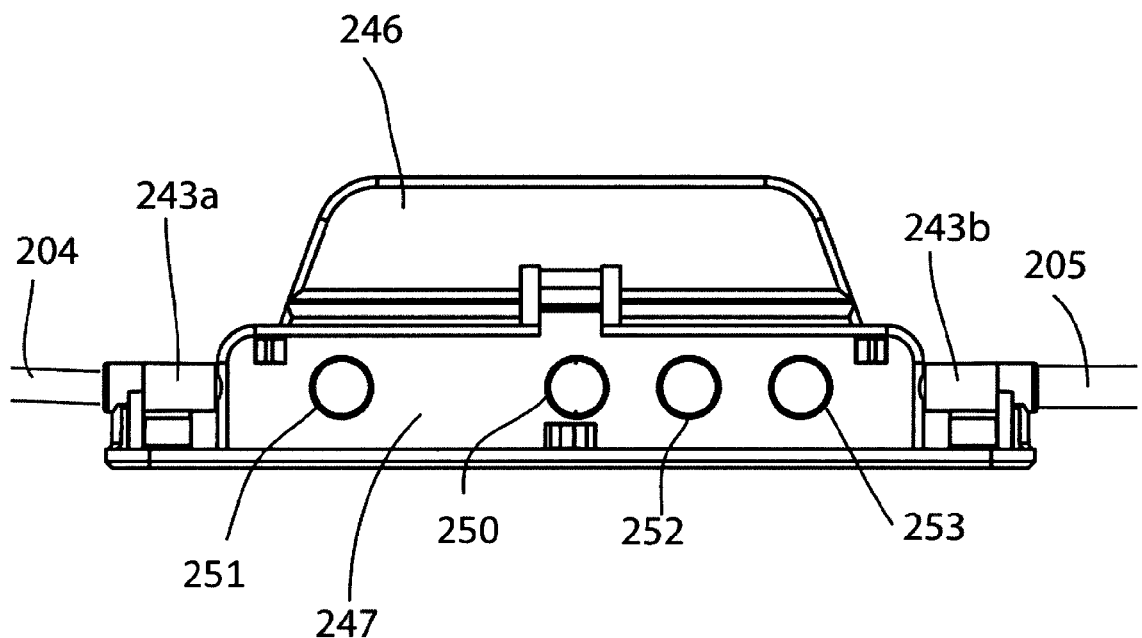
Figure 3E:
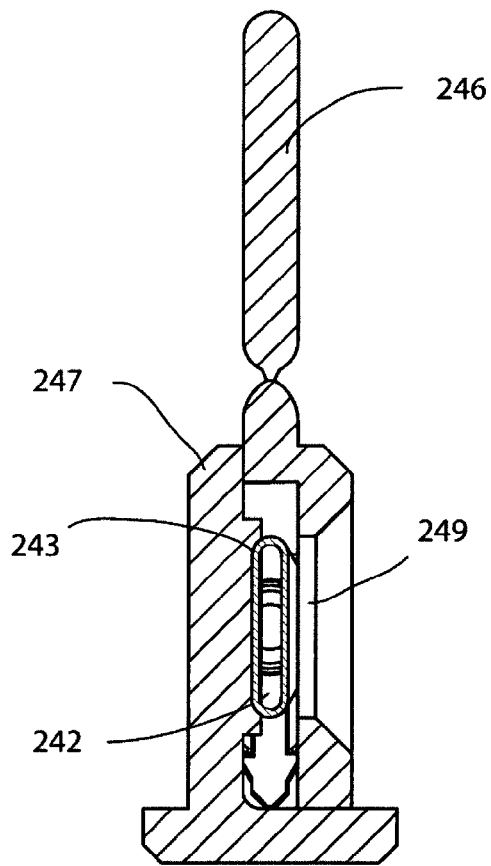
FIG. 3E is a cross-sectional view of the Flow Cell illustrated in FIG. 3C along A-A.

During operation, when Flow Cell 200 is inserted into the slot 103 of the Flow Detection Unit 100, the thermal source 109 and thermal sensors 110, 111, 112 and 113 are aligned to the windows portions 249, 250, 251, 252 and 253, respectively, that are disposed along the flow direction of the fluid through the Flow Cell 200 (FIG. 2B and FIG. 3B. The window portions 249, 250, 251, 252 and 253 may be openings formed on one or both of first and second plates 246 and 247, transparent panels and/or other suitable configurations that allow thermal radiation to be transmitted between the fluid in the Flow Cell 200 and the thermal source 109 and sensors 100, 111, 112 and 113 through first and second plates 246 and 247, without substantial thermal energy losses. The slot 103 (FIG. 2) provides simplicity and ease of use for attaching Flow Cell 200 to Flow Detection Unit 100, thus obviating the need for additional protective means to prevent unintended visual and physical exposure to the radiation waves from the thermal source 109.

In one embodiment, the Flow Cell 200 may be bar-coded and together with a bar code reading feature, hence the need for manual user inputs may be obviated. In an embodiment of the invention, the Flow Detection Unit 100 comprises a barcode reading/scanning means 114 to read a barcode 312 on the Flow Cell 200 as the Flow Cell 200 is inserted into and swiped along the slot 103. The barcode 312 can be encrypted by a commercially available printer, a laser marking system or other means onto the Flow Cell 200. In one embodiment, the barcode reading means 114 is a photocell comprising emitter and receiver elements for sensing the barcode 312 as the Flow Cell 200 is swiped along the slot 103. The orientation of the barcode reading means 114 in relation to the slot 103 may differ from the illustrations in the context and in the drawings, depending on the barcode position marked on the Flow Cell 200. Upon reading the barcode 312, the barcode scanning means 114 generates an input signal to a microprocessor or micro-controller unit (MCU) 130 in the Flow Detection Unit 100. The input signal can be used to, for example, set the reference value for calculation of flow rates, infused volume as well as the interval frequency of the thermal pulses (or heat pulses) to be emitted by thermal source 109.

In one embodiment, the display screen 108 is activated to request user for inputs of flow rate and fill volume when the barcode reading means 114 failed to generate input signals for MCU 130 after reading the barcode 312, or in a situation when wireless transmission of such data from a server to the Flow Detection Unit 100 failed. In one embodiment, the Flow Detection Unit 100 comprises a membrane switch 107 or any other forms of user input/control means, such as a scroll wheel which allows user to select predetermined values shown in the display screen 108. Alternatively, the display screen 108 may show in-screen options that allow user selection, i.e. touch-screen features to allow user input or selection.

In one embodiment, the Flow Detection Unit 100 includes a housing 102 having a top lid 120 and a bottom shell 121. For clarity purposes and to illustrate other components of Flow Detection Unit 100, the top lid 120 is not shown in FIG. 2C. In one embodiment, the Flow Detection Unit 100 comprises a power source 131 for the MCU 130, display screen 108, alarm button 104 and any associated electrical components. For example, the power source 131 can be a Lithium polymer or Lithium Ion cells or any other commercially available batteries. The power source 131 can be retained within the bottom shell 121 by a hinged cover 122 over an opening 123. Alternatively, the power source 131 could be connected to a universal serial bus (USB) port for charging on board.

In an embodiment of the invention, the power source 131 can be coupled to an electrical port 116, for example a USB port, which may be used to recharge the power source 131. The electrical port 116 can also be configured to serve as a communication port to store data in the MCU 130, for example, from a pen scanner. In another embodiment, the electrical port 116 receives data from a scanning wand or any equivalent barcode input, where the data could be patient and medication information that are automatically stored in the MCU 130. These data could be retrieved using the membrane switch 107 and used as positive identification purposes for patient-drug patency.

In an embodiment of the invention, the Flow Detection Unit 100 may be equipped with wireless connectivity means 105, e.g. a blue tooth or wifi device etc., to allow data exchange between itself and a remote server 35 wirelessly (FIG. 2A). In one application, the server could send patient and medication data to the Flow Detection Unit 100 when the Flow Cell 200 is swiped or attached to it. This feature allows the caregiver to confirm that the infusion system comprising the Flow Cell 200 as a segment of the fluid channel carries the correct medication to the patient. Likewise, any adverse events pertaining to infusion irregularities or any event that may require imminent attention could be communicated remotely to the server, hence allowing care givers to plan and schedule work ahead. The possibilities arising from wireless connectivity associated with the means of monitoring status of infusion as described in this invention is encompassing for anyone ordinarily skilled in the art.

The Flow Cell 200 forms a segment of the fluid path from the fluid source 201 to the patient 20, either as an integral part of the infusion system or as a separate standalone component that is connected to the infusion system. In a preferred embodiment, the Flow Cell 200 is flat paneled in shape. Referring to FIGS. 3A-3E, the flow Cell 200 includes a tubular member, e.g. a soft flexible tube 243, a first plate 246 and a second plate 247. Soft flexible tube 243 defines a fluid channel 241 therethrough. First and second plates 246 and 247 are constructed with substantially rigid material. When assembled together, first and second plates 246 and 247 form a space therebetween which is narrower than an external diameter of soft flexible tube 243. Accordingly, first and second plates 246 and 247 press against soft flexible tube 243 disposed between plates 246 and 247. As plates 246 and 247 are rigid, soft flexible tube 243 is compressed into a thin channel shaped configuration from its original round cross sectional geometry in the section where plates 246 and 247 and soft flexible tube 243 are in contact. The rigid plates 246 and 247 are held firmly together by means of claws 254, 255 and 256 and adjacent openings or slots 257, 258 and 259 such that these features will engage each other to produce a locking action when the plates 246 and 247 are firmly pressed against each other. The positions and number of claws and slots may vary from those shown in the drawings and maybe subject to tool design considerations suitable for manufacturing. Connection of first and second plates 246, 247 by the claws and openings also enables easy assembly and when necessary, also allows first and second plates 246, 247 to be detached from each other for, e.g. checking or replacement of soft flexible tube 243. Compressed by plates 246 and 247, the cross section of the soft flexible tube 243 along a direction perpendicular to the fluid path it communicates is approximately a thin rectangular space 242 with a thickness of about 0.05 to 0.35 mm and is created between the inner walls of the soft flexible tube 243. Second plate 247 may have a slightly raised section 248 facing first plate 246. Raised section 248 is to provide uniform compression displacement onto the soft flexible tube 243. The soft flexible tube 243 is typically constructed from materials that allow transmission and detection of infrared radiation through its walls. The plates 246 and 247 could also be part of a clamp shell or hinged-like contraption as a means to achieve a thin channel-like cross section in the soft flexible tube 243 such that the fluid channel created allows thermal radiation to be transmitted to and from the fluid in a manner and extent that data could be recorded and used to develop an algorithm for flow rate determination.

Window portion 249 formed on first plate 246 may be the type of thin panel to give improved proximity or an opening to allow direct access and physical contact between the heat source 109 and the soft flexible tube 243. Window portions 250, 251, 252 and 253 formed on second plate 247 may also be the types of thin panels or openings at locations adjacent to the thermal sensors 110, 111, 112 and 113 in the Flow Detection Unit 100, to allow direct access and physical contact between thermal sensors 110, 111, 112 and 113 and soft flexible tube 243.

The soft flexible tube 243 has an inlet 243a for coupling to the fluid source 201 via inlet tube 204, and an outlet 243b for coupling to outlet tube 205. On the sidewall of soft flexible tube 243, there are defined thermal conductive portions 243c, 243d, 243e, 243f and 243g. When soft flexible tube 243 is sandwiched between first and second plates 246 and 247, thermal conductive portion 243c is in alignment with, and become at least partially overlapped to, window portion 249. Similarly, thermal conductive portions 243d, 243e, 243f and 243g are also in alignment with, and become at least partially overlapped with, window portions 250, 251, 252 and 253, respectively. This structure allows thermal signals to transmit between Flow Detection Unit 100 and Flow Cell 200 through thermal conductive portions 243c, 243d, 243e, 243f and 243g, when Flow Cell 200 is attached to Flow Detection Unit 100 and that thermal source 109, first, second, third and fourth thermal sensors 110, 111, 112 and 113 face respective window portions, 249, 250, 251, 252 and 253.

Outlet tube 205 can be coupled to a patient 20 through common means like a patient connector and catheter. The inlet 243a and outlet 243b are also means to allow improved manufacturability when the soft flexible tube 243 and the fluid tubes 204 and 205 are of different dimensions (primarily inner and/or outer diameters) or materials. The soft flexible tube 243 and fluid tubes 204 and 205 could also be connected directly without separately formed inlet 243a and outlet 243b.

Figure 3F:
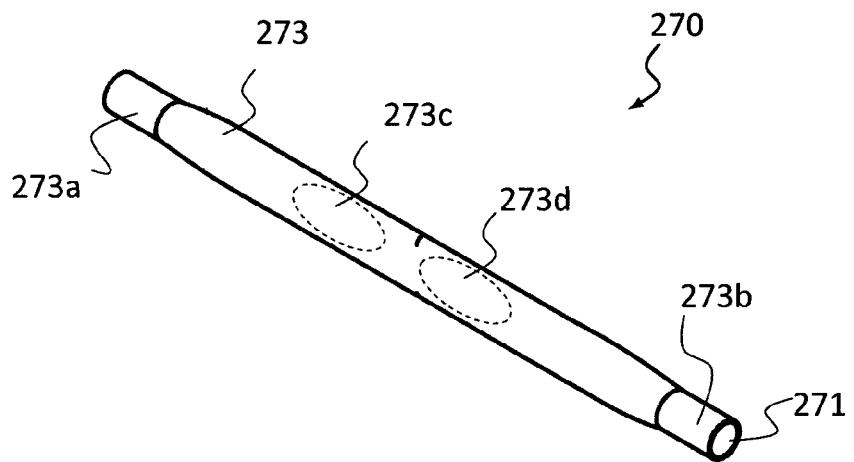
FIG. 3F is a perspective view showing a Flow Cell according to another embodiment of the present invention.

According to another embodiment of the present invention, as shown in FIG. 3F, there is provided a Flow Cell in the form of a tubular member 270 to enable thermal signal transmission with an external device, e.g. a Flow Detection Unit, for flow rate measurement, detection and monitoring in a fluid delivery system e.g. an intravenous infusion system. Tubular member 270 includes a sidewall 273 surrounding a fluid channel 271. Tubular member 270 may form a segment of a fluid path of a fluid delivery system, e.g. an intravenous infusion system. Tubular member has an inlet 273a at one end of sidewall 273, and an outlet 273b at opposite end of sidewall 273, and allows fluid to flow through fluid channel 271 from inlet 273a to outlet 273b. Sidewall 273 has a first portion 273c and a second portion 273d adjacent to first portion 273c. First portion 273c is to allow a first thermal signal to transmit into fluid channel 271, and second portion is to allow a second thermal signal to transmit out from fluid channel 271. It should be appreciated that although shown in FIG. 3F as separate regions on sidewall 273, first portion 273c and second portion 273d may also join together as one region.

Figure 3G:
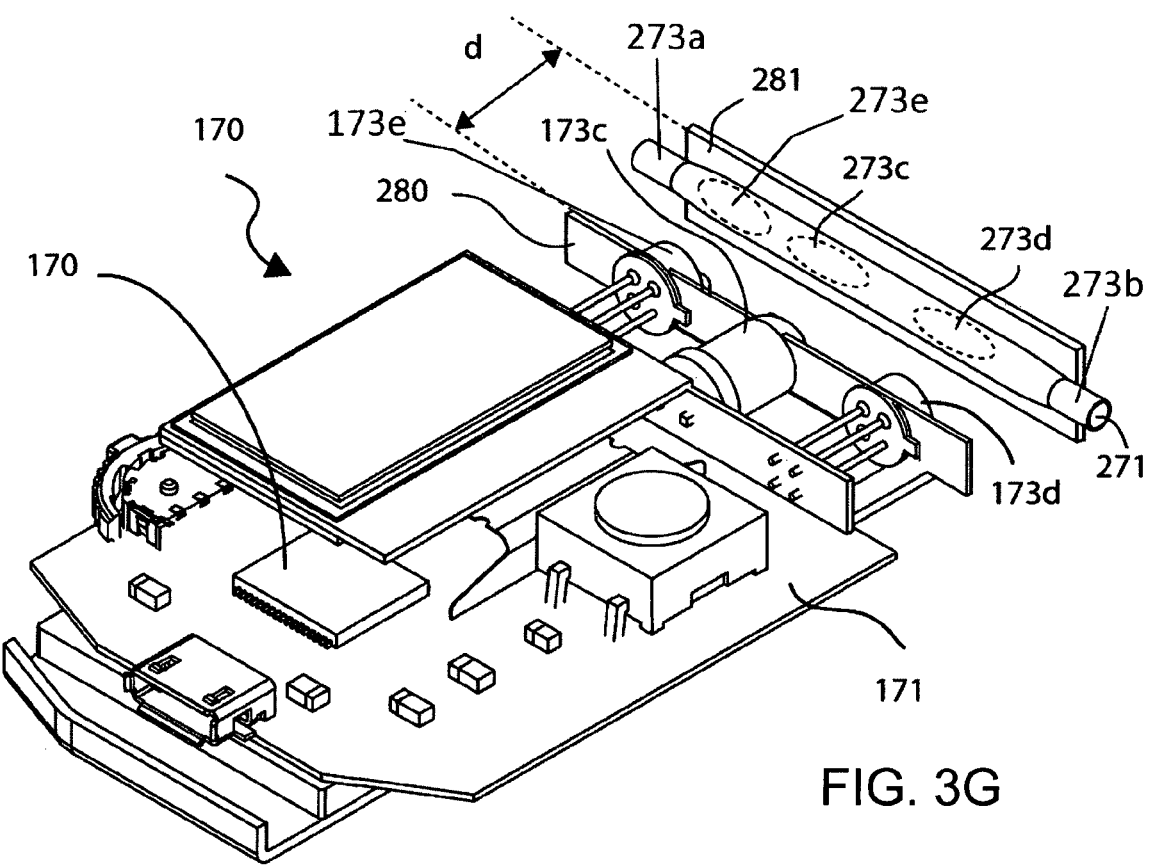
FIG. 3G is a perspective view showing a Flow Detection Unit and the Flow Cell of FIG. 3F.

FIG. 3G shows a flow detection unit 170 for flow rate detection using tubular member 270 shown in FIG. 3F. Flow detection unit 170 includes a housing 171, a thermal source 173c, a thermal sensor 173d and a controller e.g. a microprocessor 172 disposed in housing 171. Microprocessor 172 is coupled to thermal source 173c and thermal sensor 173d. In use, tubular member 270 is placed proximate to flow detection unit 170 by, e.g. attaching to housing 171 of flow detection unit 170 such that thermal source 173c is aligned with first portion 273c, and thermal sensor 173d is aligned with second portion 273d. When activated, thermal source 173c emits a first thermal signal into fluid channel 271 through first portion 273c. Meanwhile or subsequently, thermal sensor 173d receives a second thermal signal from fluid channel 271 through second portion 273d. First and second thermal signals, the time instant at which the thermal signals are emitted/ received as well as the time intervals taken in between may then be recorded by microprocessor 172 for determining the flow rate based on methods as hereinafter described.

Housing 171 may have a first plate 280 on which thermal source 173c and first thermal sensor 173d are fixed, and a second plate 281 opposite to first plate 280. First plate 280 is fixed to housing 171, second plate 281 is movable relative to first plate 280. When second plate 281 is at a position away from first plate 280, e.g. with a distance d greater than an external diameter of tubular member 270, tubular member 270 can be placed between first plate 280 and second plate 281. When second plate 281 move towards first plate 280, i.e. by decreasing distance d, tubular member 270 will be clamped between first and second plates 280, 281 such that tubular member 270 is fixed to housing 171. At this position, first portion 273c is aligned with thermal source 173c, and second portion 273d is aligned with first thermal sensor 173d such that, a first thermal signal from thermal source 173c can be emitted into tubular member 270 through first portion 273c, and a second thermal signal from tubular member 270 through second portion 273d can be received by second thermal sensor 173d.

Flow detection unit 170 may include a second thermal sensor 173e disposed at the opposite side of first thermal sensor 173d about thermal source 173c. Tubular member 270 includes a third portion 273e between inlet 273a and first portion 273c. When tubular member 270 is clamped between first plate 280 and second plate 281, third portion 273e is aligned with second thermal sensor 173e such that a third thermal signal from tubular member 270 through third portion 273e can be received by second thermal sensor 173e.

Figure 4A:
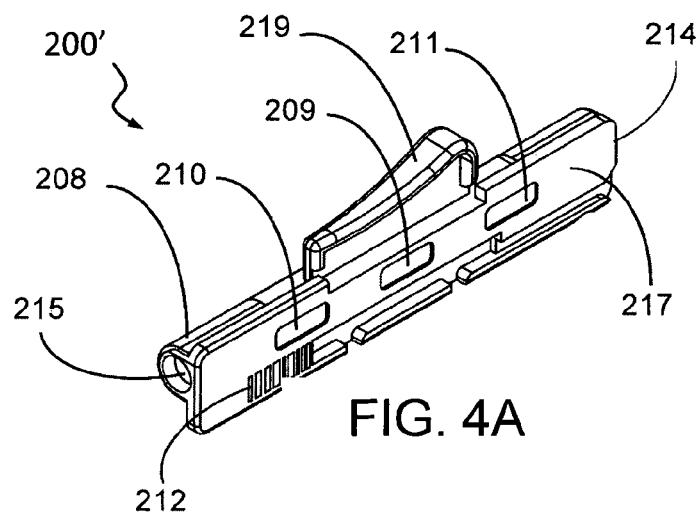
FIG. 4A is a perspective view of a Flow Cell in accordance with yet another embodiment of the invention.
Figure 4D:
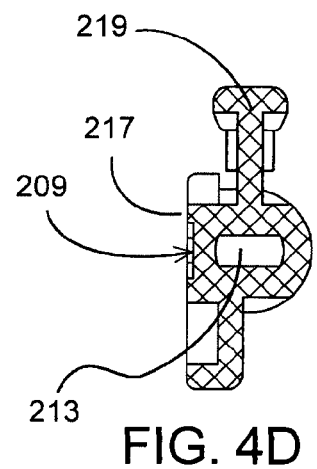
FIG. 4D is a cross-sectional view of the Flow Cell taken along line A-A in FIG. 4B.
Figure 4B:
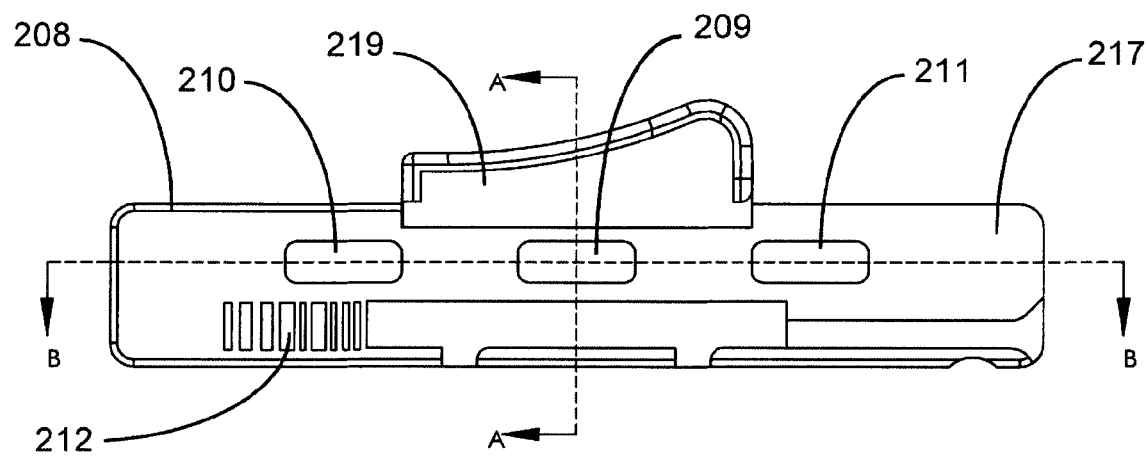
FIG. 4B is a side view of the Flow Cell illustrated in FIG. 4A.
Figure 4C:
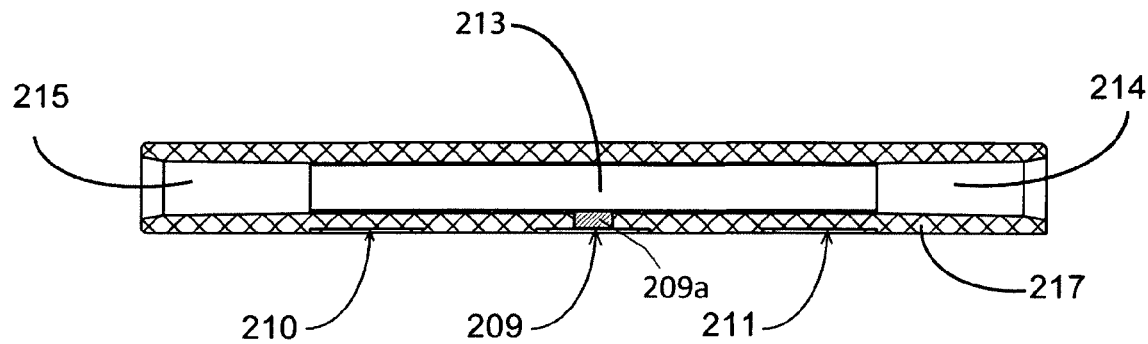
FIG. 4C is a cross-sectional view of the Flow Cell taken along line B-B in FIG. 4B.
Figure 4E:
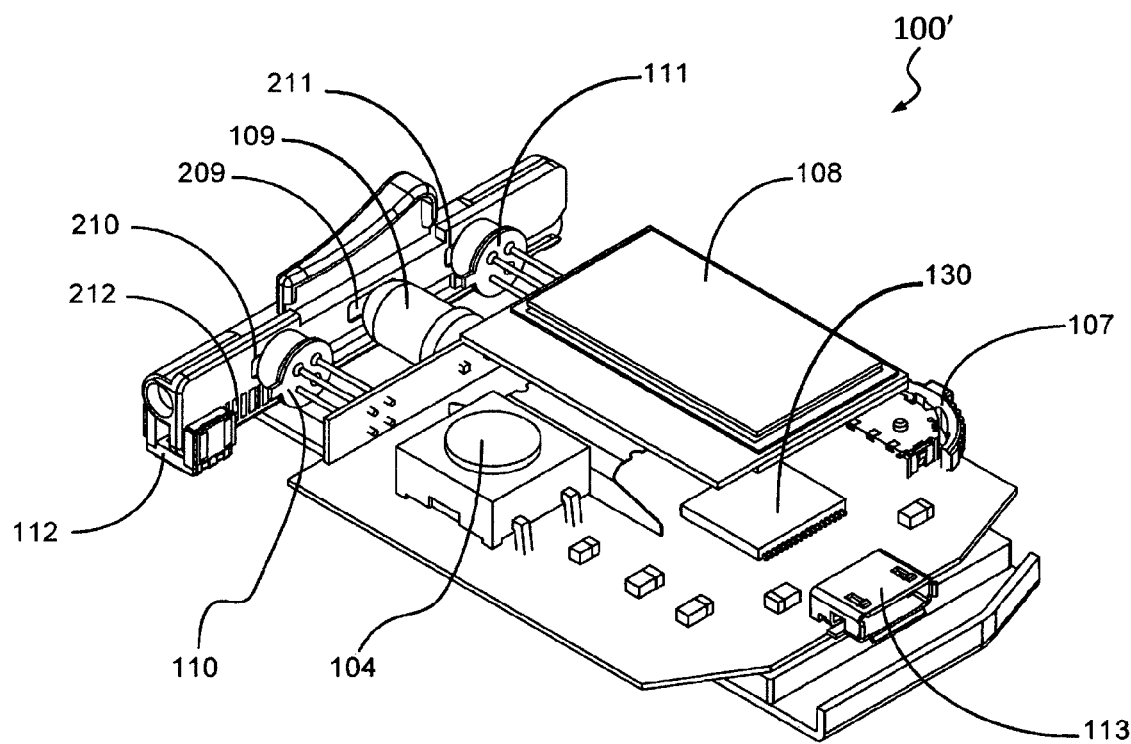
FIG. 4E is a perspective view of a Flow Detection Unit in use with the flow cell shown in FIG. 4A in accordance with one embodiment of the invention.
Figure 5A:
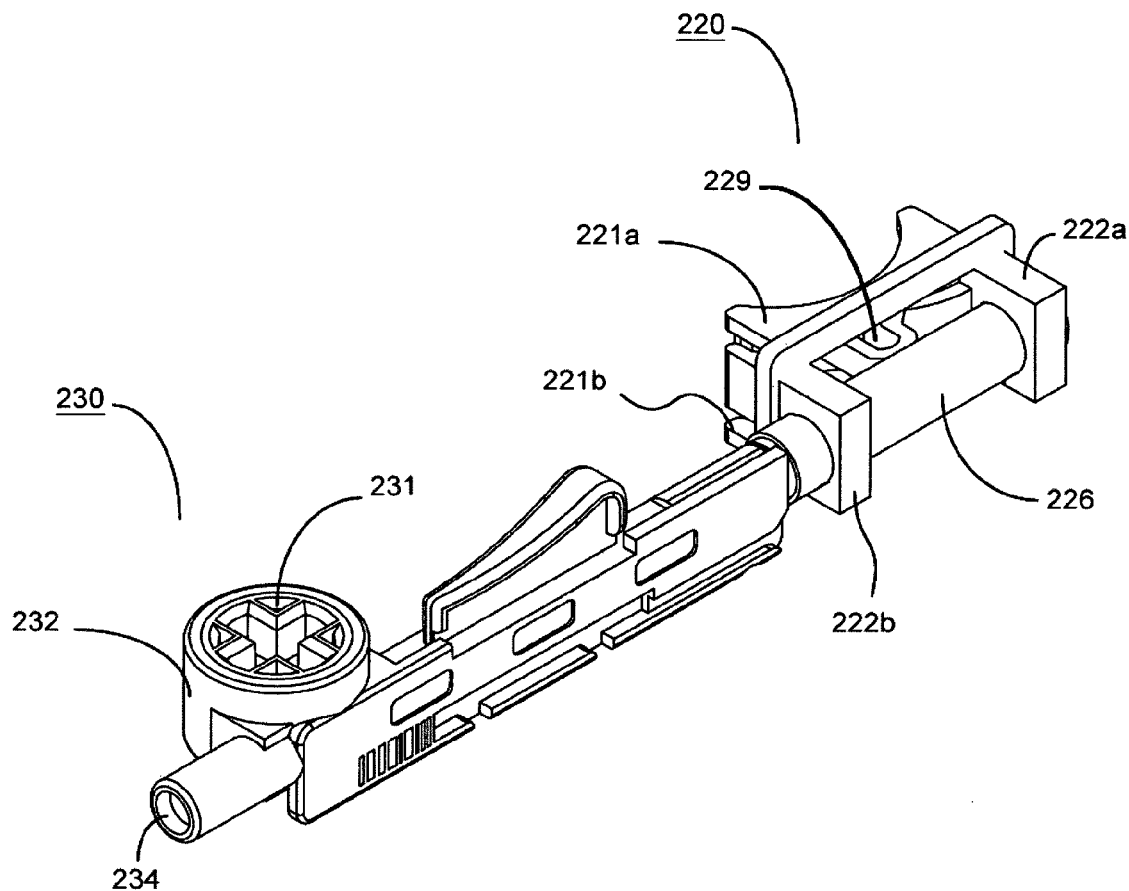
FIG. 5A is a perspective view of the Flow Cell shown in FIG. 4A coupled to a flow regulating mechanism and a clamping mechanism in accordance with one embodiment of the invention.
Figure 5B:
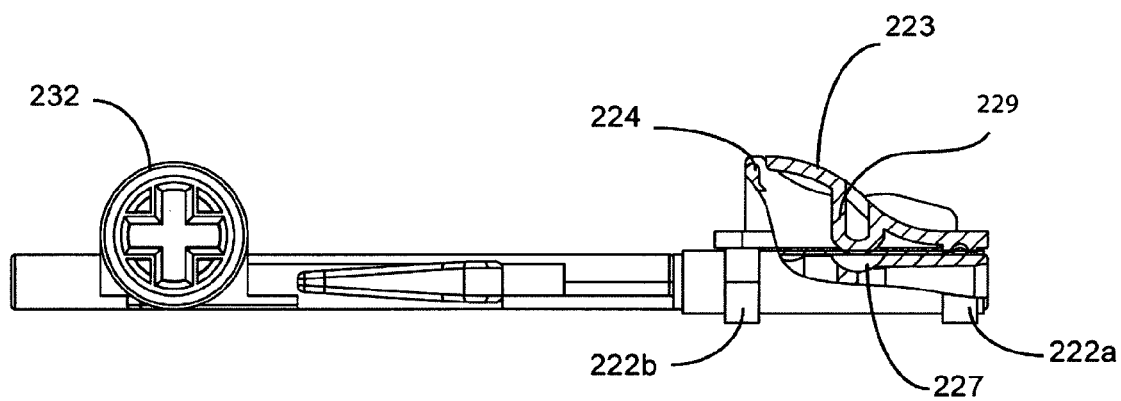
FIG. 5B is a top view of the Flow Cell shown in FIG. 5A with a partial cross-sectional view of the clamping mechanism.
Figure 5C:
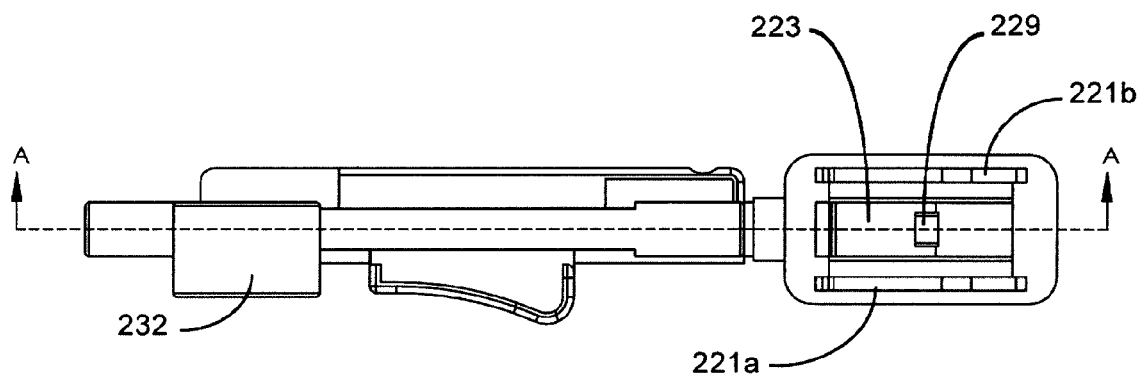
FIG. 5C is a side view of the Flow Cell illustrated in FIG. 5A.
Figure 5D:
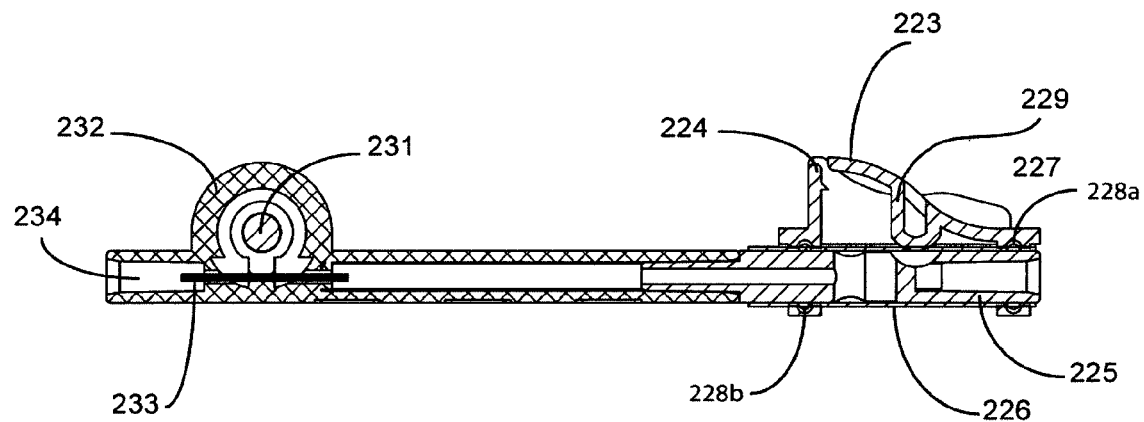
FIG. 5D is a cross-sectional view of the Flow Cell viewed from the line A-A in FIG. 5C.

In a further embodiment, as shown in FIGS. 4A-4E, a Flow Cell 200' is tubular in shape and comprises a housing 208 having an inlet 214, an outlet 215, and a fluid channel 213 in fluid communication with the inlet 214 and outlet 215. Housing 208 is formed of rigid material, by injection molding for instance. Housing 208 includes a sidewall 217 defining the channel 213, and with three window portions 209, 210, 211 formed on sidewall 217. The window portion 209 allows thermal energy to be transmitted to the fluid flowing through channel 213, at the window portion 209 of the channel 213. The window portions 210 and 211 allow the detection of respective thermal energy levels (i.e. temperature) of the fluid at the window portions 210 and 211. When the Flow Cell 200' is attached to a Flow Detection Unit, e.g. a Flow Detection Unit 100' shown in FIG. 4E, the window portions 210, 211 and 209 are substantially aligned to the thermal sensors 110, 111 and thermal source 109 respectively (FIG. 4E). In one embodiment, the housing 208 of the Flow Cell 200' includes a protrusion or handle 219 that eases the insertion or removal of the Flow Cell 200' into/from the slot 103 of the Flow Detection Unit 100'.

In one embodiment where the thermal source 109 utilizes an IR diode, the Flow Cell 200' can be made from materials with minimal IR absorption characteristics. In other words, Flow Cell 200' can be made of materials that allow a large percentage of the IR radiation to be transmitted to the fluid. For example, the window portions 209,210, 211 are made of polyethylene materials. Alternatively, the entire Flow Cell 200' can be made of polycarbonate materials. In another embodiment, the window portions 209, 210, 211 are each formed as a recess on the sidewall 217 such that the window portions 209, 210, 211 have smaller thickness than the other portions of the sidewall 217. The smaller thickness helps to reduce the absorption of radiation by the window portions 209, 210, 211.

If a laser diode is used as the thermal source 109, heat transfer probes 209a (only one is shown) may be used to improve the transfer of heat to the fluid in the channel 213, as shown in FIG. 4C. The probes are made of good heat conducting material, e.g. stainless steel, and at least one probe is integrated into each of the window portions 209, 210, 211, for example by insert molding techniques. The probe 209a extends across the thickness of portion 209 such that it has an exposed surface in contact or in close proximity to the thermal source 109 when the heat pulse is emitted, and an opposite surface in contact with the fluid path so that the fluid receives the heat pulses. Similarly, probes at the portions 210 and 211 has an exposed surface in contact or in close proximity to the thermal sensors 110 and 111, and opposite surfaces in contact with the fluid to conduct heat from the fluid to the thermal sensors 110 and 111.

In one embodiment, the Flow Cell 200, 270 or 200' may include a clamping mechanism 220 at one end, for example at the inlet 214, and a flow rate regulating mechanism 230 at the other end, for example the outlet 215 (FIGS. 5A-5D). The clamping mechanism 220 offers a means of stopping fluid flow from the fluid source 201 to the patient 20, while the flow regulating mechanism 230 provides a means of adjusting the flow rate of the fluid. In an embodiment of the invention, the flow regulating mechanism 230 includes a barrel 232 inside which a rotatable axle 231 is disposed. A fluid tube can be coupled to the opening 234 of the flow regulating mechanism 230. Rotation of the axle 231 about its axis will move a stem 233 (solid or hollow) into the fluid tube in a longitudinal direction such that the effective lumen of the fluid tube will vary, hence modifying the flow rate of the fluid passing through it. This action of rotating the axle 231 could be done manually or by means of an actuating mechanism, for example a robotic arm interface that receives signals from the MCU 130 of the Flow Detection Unit 100 to effect the necessary rotation. The adjustment in the flow rate can be made automatically and optimized using data of the infusion stored in the Flow Detection Unit 100.

In an embodiment of the invention, the clamping mechanism 220 includes a tubular construction 225 with a silicone or pliable material as an over sleeve 226. The tubular construction 225 can be made from any hard plastics. In one embodiment, the over sleeve 226 is secured in position with respect to the tubular construction 225 by O Rings 228a and 228b (FIG. 5D) made of elastic material or any constrictive means such that the fluid path along the axis of the Flow Cell 200 is not compromised due to leakages. The O Rings 228a, 228b can be protected by retainers 222a and 222b which may be designed to be part of a single molded piece. The clamping function is achieved by a lever 223 which includes a protrusion 229 on its underside. When the lever 223 is pushed towards the over sleeve 226, the protrusion 229 will press against the wall of the over sleeve 226. There is a notch 227 that permits the protrusion 229 to extend into the tubular construction 225 and cause a partial or full blockage of the fluid flow. The lever 223, when pushed downwards, is held in place by a catch 224. The lever 223 can be released by pushing the catch 224 away from the lever 223. To avoid accidental activation of the lever 223, there are side shields 221a and 221b formed on both sides of the lever 223.

The use of the clamping mechanism 220 and flow regulating mechanism 230 allows the function of stopping or regulating flow to be grouped within close proximity to the Flow Cell 200, hence offering convenience for the healthcare provider. However, it can be appreciated that the Flow Cell 200 can be used without the clamping mechanism 220 or flow regulating mechanism 230.

FIG. 6A to FIG. 6D illustrate an exemplary temperature vs. time graphs according to embodiments of the present invention, e.g. for the temperature readings by the thermal sensors 110 and 111 of Flow Detection Unit 100 shown in FIG. 4E. Taken from a direction of flow of the fluid to be measured, thermal sensor 110 is situated in a downstream position in relation to the thermal source 109, while thermal sensor 111 is situated upstream in relation to thermal source 109.

Figure 6A:
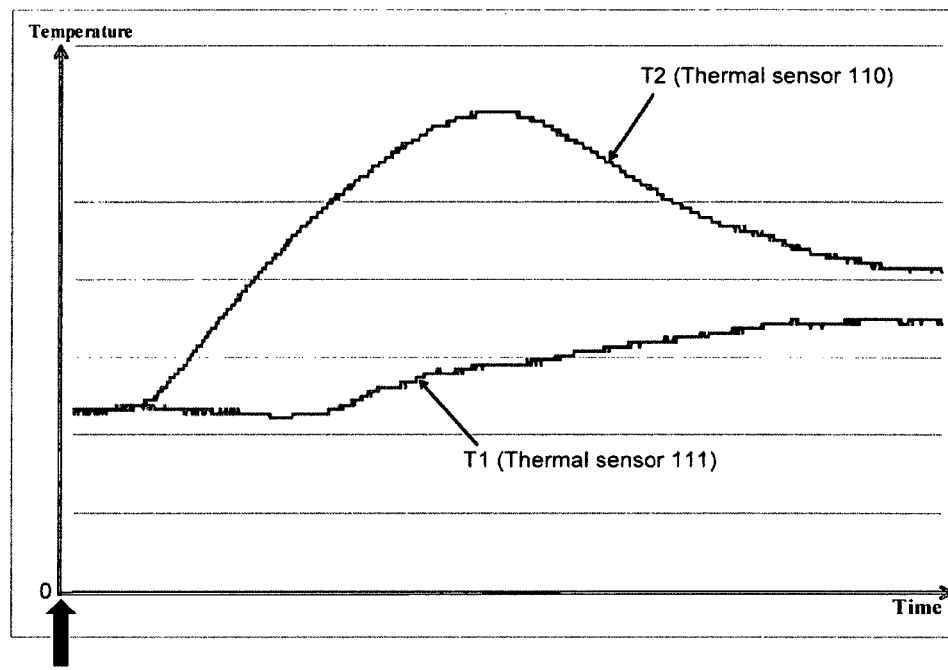
FIGS. 6A and 6B are examples of temperature vs time graphs of the temperature profiles in the Flow Cell.
Figure 6B:
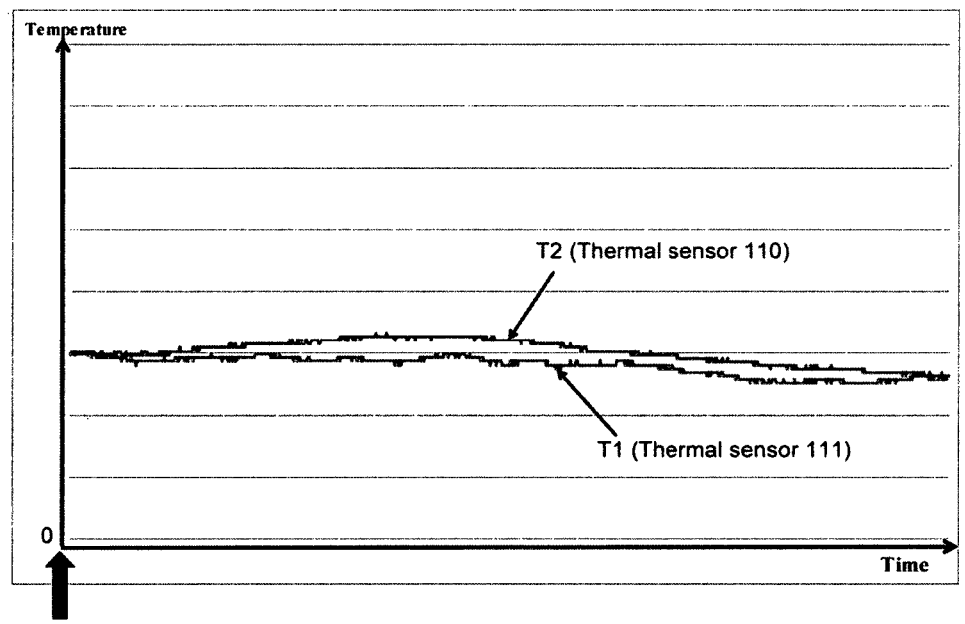

The temperature readings detected at thermal sensor 110 (represented by line T2) and at thermal sensor 111 (represented by line T1) vary according to the thermo diffusion of the fluid heated by thermal source 109 and also the flow of fluid passing through the thermal sensors 110, 111 locations in the channel 213. In FIG. 6A, the temperature T2 is higher than T1 as the fluid passing thermal sensor 110 would have predominantly being heated by thermal source 109, while the temperature T1 would represent the temperature of fluid at thermal sensor 111 before it is heated by thermal source 109. Measuring the difference in the temperatures T2 and T1 allows the confirmation of flow of fluid. In a similar fashion, the minimal or lack of temperature difference between T2 and T1 is an indication of no flow or an occurrence of occlusion (see FIG. 6B and FIG. 6C).

Figure 6C:
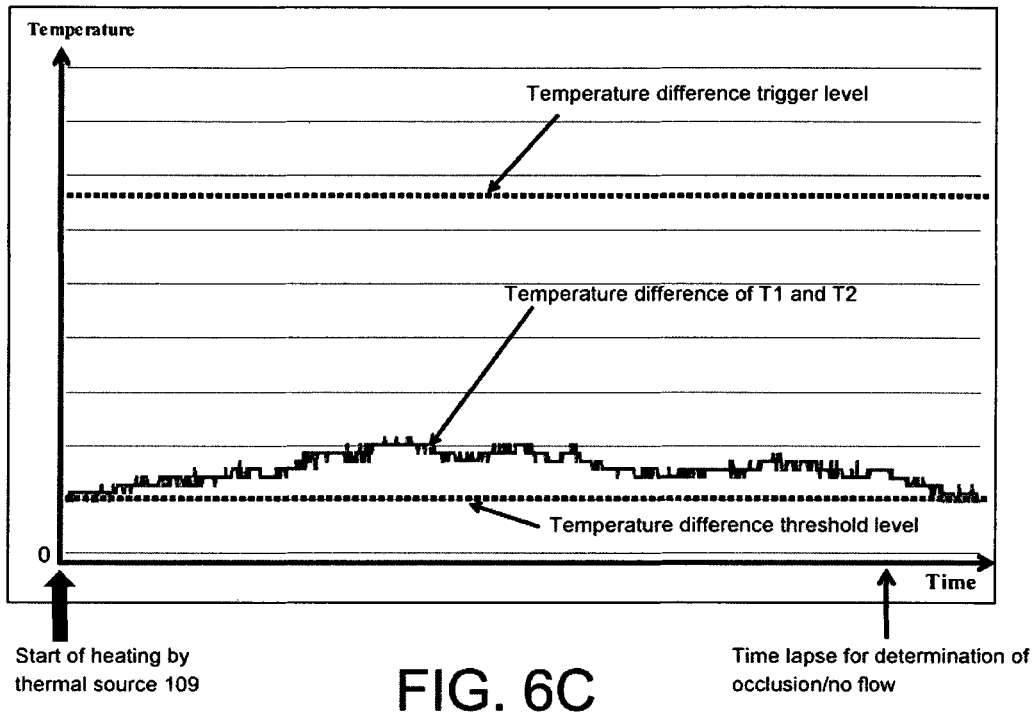
FIGS. 6C and 6D are examples of temperature vs. time graphs of the temperature difference in the Flow Cell.
Figure 6D:
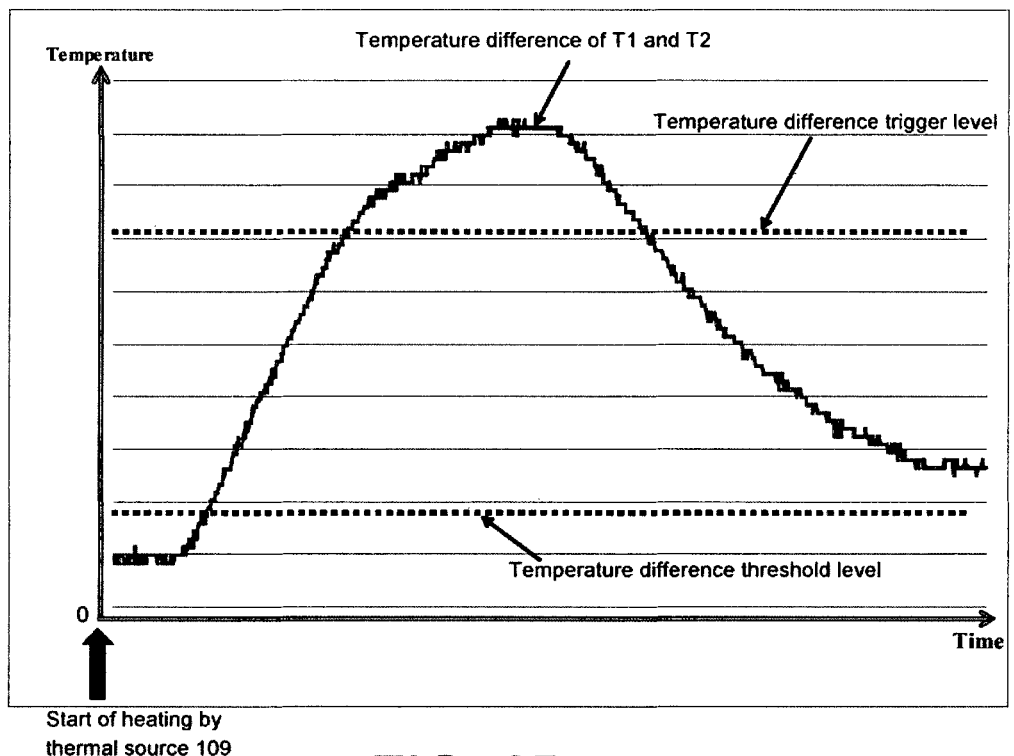

Further referring to FIG. 6C, a temperature difference threshold level representing a predetermined quantum in the differential in temperatures between T2 and T1 could be used to determine flow or no flow situations. This threshold level could also be used, in conjunction with the thermal pulse duration of the thermal source 109 to determine the flow rate of the fluid passing through the channel 213. The fluid passing through the channel 213 or alternatively thin rectangular space 242 acts as a carrier of thermal energy or heat emitted by the thermal source 109. The time taken for the fluid heated by the thermal source 109 to pass through fixed distance between thermal source 109 and thermal sensor 110 will be measured and the electronic circuitry of the Flow Detection Unit 100 can be designed to have repetitions of such measurements to achieve better accuracy. Since the cross section of the fluid path (i.e. channel 213) in the Flow Cell 200 is fixed, the time taken for the thermal pulse to appear at thermal sensor 111, or to flow cells with more sensors e.g. thermal sensors 112 or 113, and the amplitude of such a thermal pulse at each of the sensor locations would vary according to the flow rate of the fluid And could be determined. In similar fashion, the approximate volume of fluid delivered can be derived from the flow rate and duration lapsed. Trigger level is a predetermined reference level to ensure that time measurements are consistent, i.e. time is measured when this level is reached.

Figure 7:
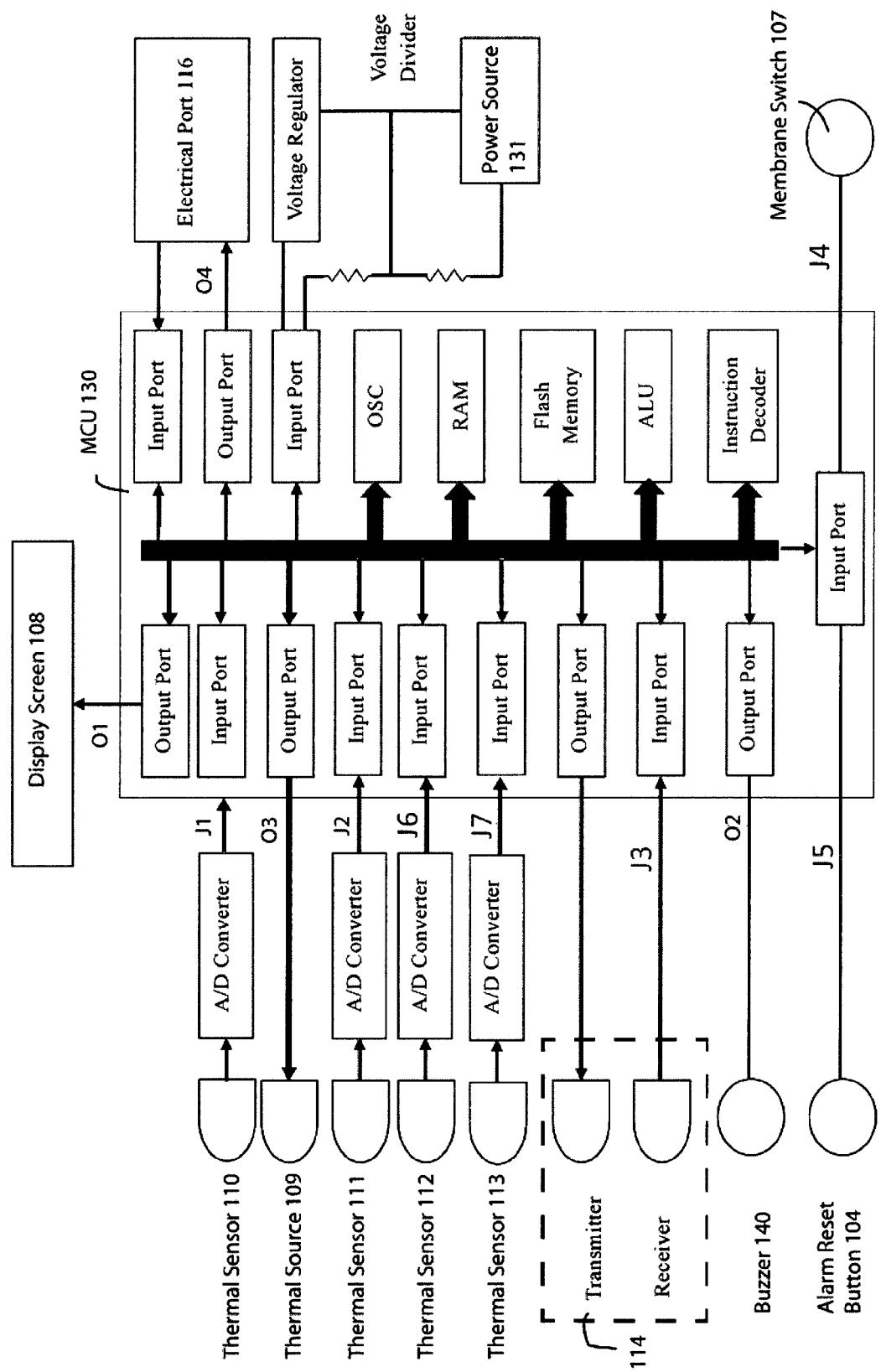
FIG. 7 is a block diagram of the Flow Detection Unit in accordance with an embodiment of the invention.

Referring to FIG. 7, input ports of MCU 130 receive a signal J1 from thermal sensor 110, a signal J2 from thermal sensor 111, and a signal J3 from the barcode reading means 114, a signal J4 from membrane switch 107 and an alarm reset signal J5 from alarm button 104. In embodiments having more thermal sensors, e.g. thermal sensor 112, 113, MCU 130 also receive signals J6 and 17 from respective thermal sensors 112 and 113. A display latch and driver controls the display screen 108. The MCU 130 sends signals O1 to display screen 108, O2 to a buzzer 140 to indicate occlusion, end of infusion and unacceptable flow rate detected; O3 to trigger thermal source 109 to emit at a desired time interval based on the expected flow rate of the fluid in the channel 213 or alternatively channel 242. The input signal for the expected flow rate is made possible via the barcode signal J3. To conserve power consumption, a signal from the MCU 130 will control the power source 131 to operate intermittently. The power source 131 can be coupled to the MCU 130 via a voltage regulator.

A software program is stored in a Flash Memory to work with the arithmetic logic unit (ALU) to generate the output signals O1, O2, O3 and O4. O4 represents a signal to display patient data when the barcode 212, tagged to some patient data, is read by the barcode reading means 114. Signals J1 and J2 are compared and a differential is referenced with a predetermined threshold giving an output O2 when there is an occlusion. In the absence of occlusion, the time taken for J2 to reach a trigger level will produce a signal O1 which displays the flow rate in, for example, mL per hour.

Figure 8:
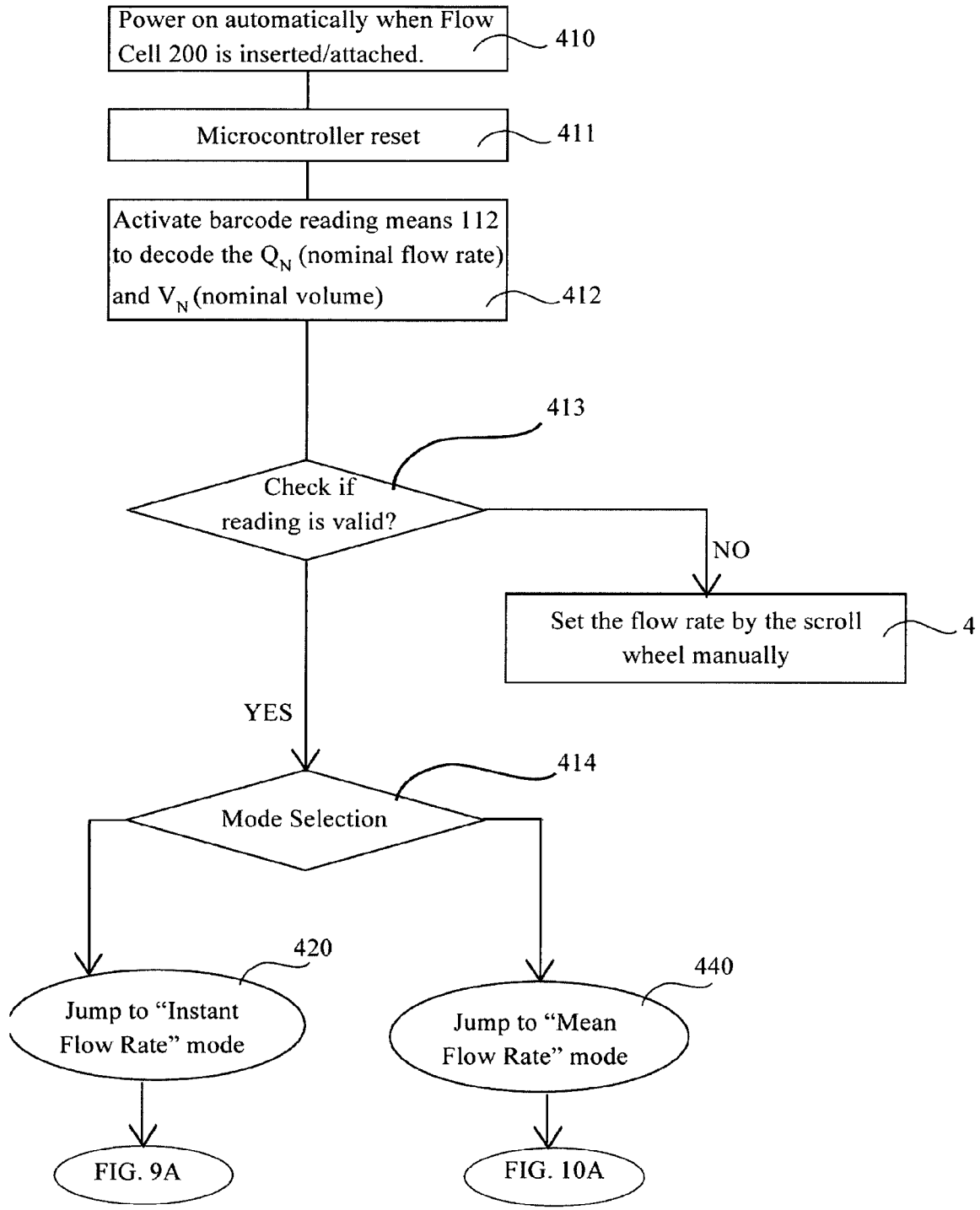
FIG. 8 is a flow diagram illustrating the functions of the Flow Detection Unit in accordance with an embodiment of the invention.

Referring to FIG. 8, in a method of detecting flow rate of intravenous fluid delivery system according to one embodiment of the present invention, the Flow Detection Unit 100 is powered on automatically when the Flow Cell 200 is inserted, e.g. inserted into an opening (or slot 103) of the Flow Detection Unit 100 or suitably attached to the Flow Detection Unit 100 (step 410). The MCU 130 then undergoes a reset (step 411) before activating the barcode reading means 114 to decode the nominal flow rate ($Q_N$) and nominal volume ($V_N$) at step 412. The barcode 212 or alternatively 312 is decoded by the barcode reading means 114 to provide nominal flow rate data ($Q_N$) as well as nominal volume ($V_N$) for calculations to be performed by the MCU 130. Data from the barcode 212 or alternatively 312 is decoded by blocking and transmitting IR light from the barcode reading means 114 during Flow Cell 200 insertion into the Flow Detection Unit 100. Next, the MCU 130 checks whether the reading or data decoded from the barcode 212 or alternatively 312 is valid (step 413). For example, the MCU 130 comprises a checksum function to ensure that any dirt or blur on the barcode 212 or alternatively 312 area does not cause wrong readings. In the event such decoding fails or the data is not valid, manual input via the membrane switch 107 will be prompted (step 415). Otherwise, the display screen 108 would display automatically a mode selection option (step 414) for instantaneous flow rate (step 420) or mean flow rate (step 440) measurements. User then selects the desired mode by manipulating the membrane switch 107.

Figure 9A:
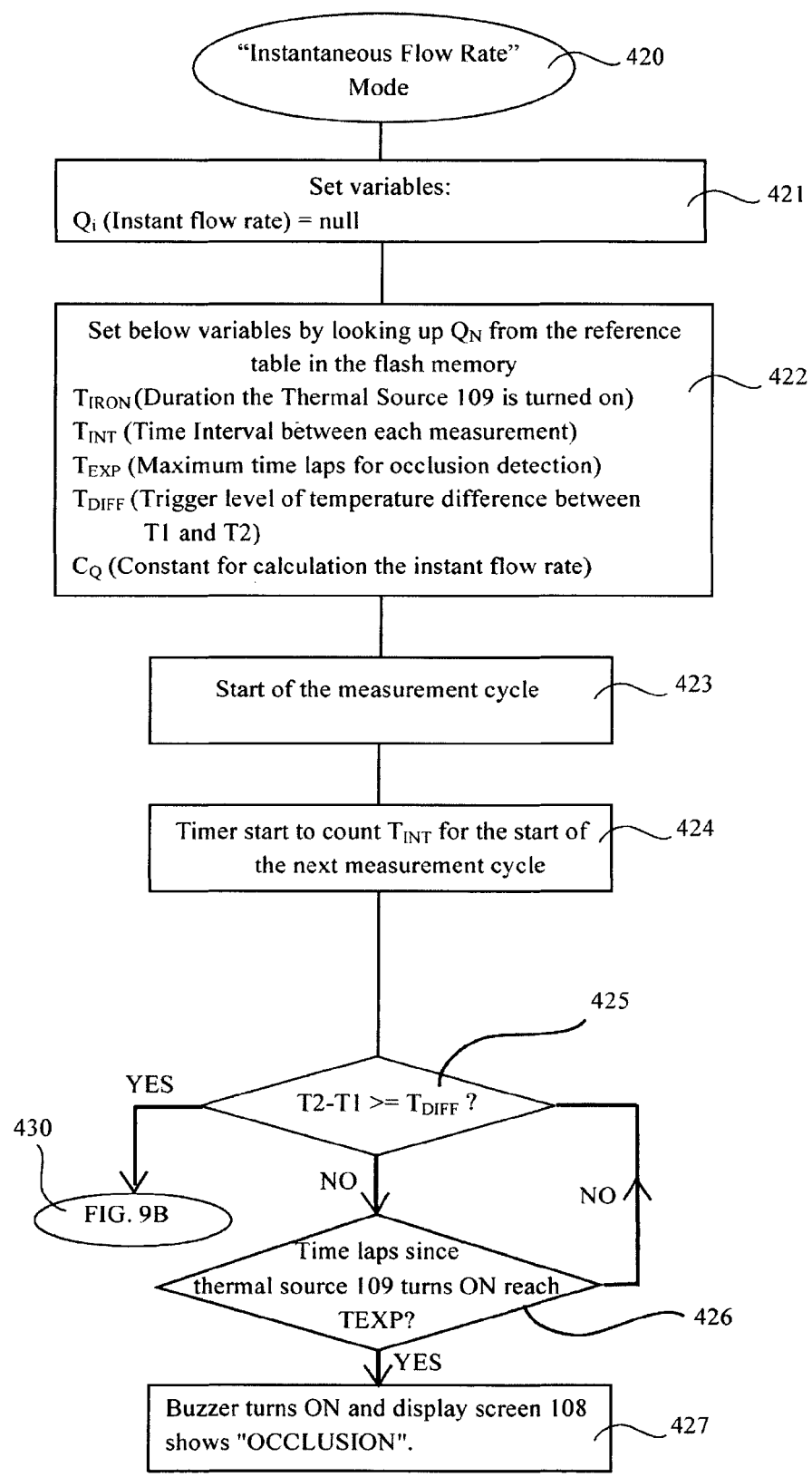
FIGS. 9A and 9B are flow diagrams illustrating the instantaneous flow rate mode in accordance with an embodiment of the invention.

Referring to FIG. 9A, the Flow Detection Unit 100 is programmed to display instantaneous flow rate (step 420). Next, the MCU 130 sets the initial instantaneous flow rate ($Q_i$) to "null" (step 421) and sets the measurement variables by looking up the nominal flow rate ($Q_N$) value from a reference table stored in the Flash Memory of the Flow Detection Unit 100 (step 422). The measurement variables comprises the duration the thermal source 109 is switched on ($T_{IRON}$), the time interval between each measurement ($T_{INT}$), the maximum time laps for detecting the presence of an occlusion ($T_{EXP}$), the trigger level of temperature difference between T1 and T2 ($T_{DIFF}$), and the constant for the calculating the instant flow rate ($C_Q$). In embodiments where the Flow Cell 200 is predisposed with more temperature measurement locations along its fluid channel, additional permutations of $T_{DIFF}$ could be developed to further improve the accuracy of flow rate determination.

When the measurement cycle starts (step 423), the thermal source 109 will be turned ON and OFF intermittently to emit heat pulses to the fluid in the channel 213. In one embodiment, the thermal source 109 turns on for the duration of $T_{IRON}$ then turns off. The temperature difference ($T_{DIFF}$) between the readings at thermal sensors 110 (T2) and 111 (T1) is measured and a timer starts to count time interval (T.sub.INT) for the start of the next measurement cycle (step 424), which helps to ensure that the measurements are taken at equal intervals. At step 425, the measured temperature difference (T2-T1) is compared against a predetermined trigger level (T.sub.DIFF) to confirm the existence of fluid flow versus occlusion. In other words, the MCU 130 checks whether the temperature difference between T1 and T2 exceeds the trigger level (T.sub.DIFF).

If there is occlusion, the difference in the temperature readings taken by thermal sensors 110 and 111 will be below the trigger level (T.sub.DIFF), which activates the buzzer/alarm on the Flow Detection Unit 100. A suitable display indicator, e.g. "OCCLUSION" will be shown on the display screen 108 (step 427). In one embodiment, the MCU 130, at step 426, checks whether the number of time laps, from the time the thermal source 109 turned on, has reached the maximum laps for occlusion detection (T.sub.EXP) before activating the buzzer at step 427. In other words, the buzzer activates after the maximum waiting time had lapsed without the temperature difference (T2-T1) reaching or exceeding the trigger level (T.sub.DIFF).

Figure 9B:
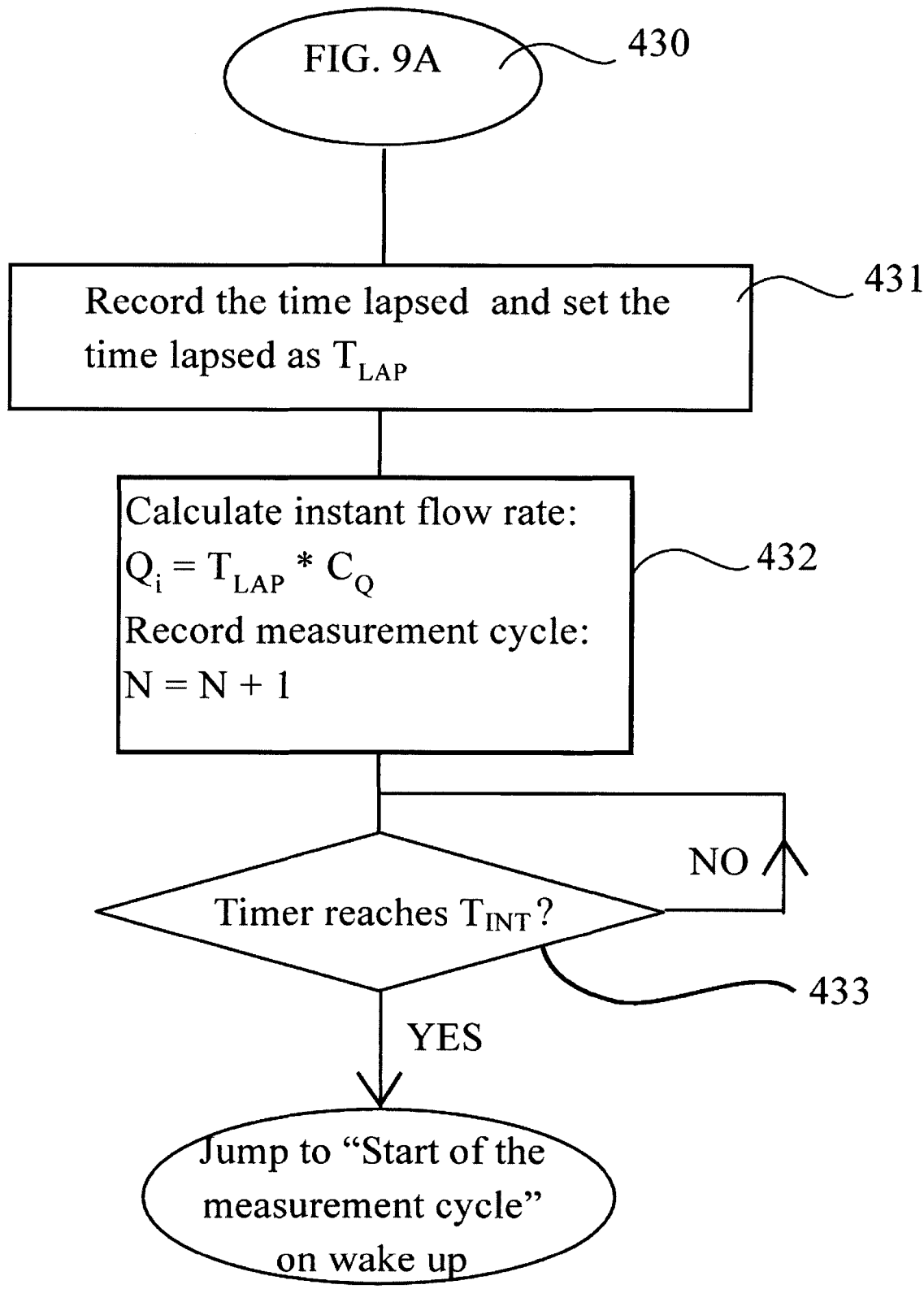

In the absence of occlusion (430), the time taken for the temperature difference (T2-T1) to reach the predetermined trigger level (T.sub.DIFF) will be measured (step 431) and stored as T.sub.LAP (step 431), and subsequent readings of this duration are taken (see FIG. 9B). In other words, the MCU 130 records the time lapsed or time duration from the moment the thermal source 109 is turned on until the temperature difference (T2-T1) reached the trigger level (T.sub.DIFF), and sets the time lapsed as T.sub.LAP. Next, at step 432, the instantaneous flow rate (Qi) is calculated as Qi=T.sub.LAP.times.C.sub.Q. The number of measurement cycle completed is represented as N=N+1, where initially N is defined as zero. A timer in the Flow Detection Unit checks whether the measurement time has reached the selected T.sub.INT (step 433), which helps to control the measurement interval. If the interval has reached a preset value of T.sub.INT, the measurement cycle restarts at step 423 in FIG. 9A. The measurement intervals are optimized to the timing of the pulses emitted by thermal source 109, and different nominal flow rate (Q.sub.N) entry registered by the MCU will result in different measurement intervals.

Figure 6E:
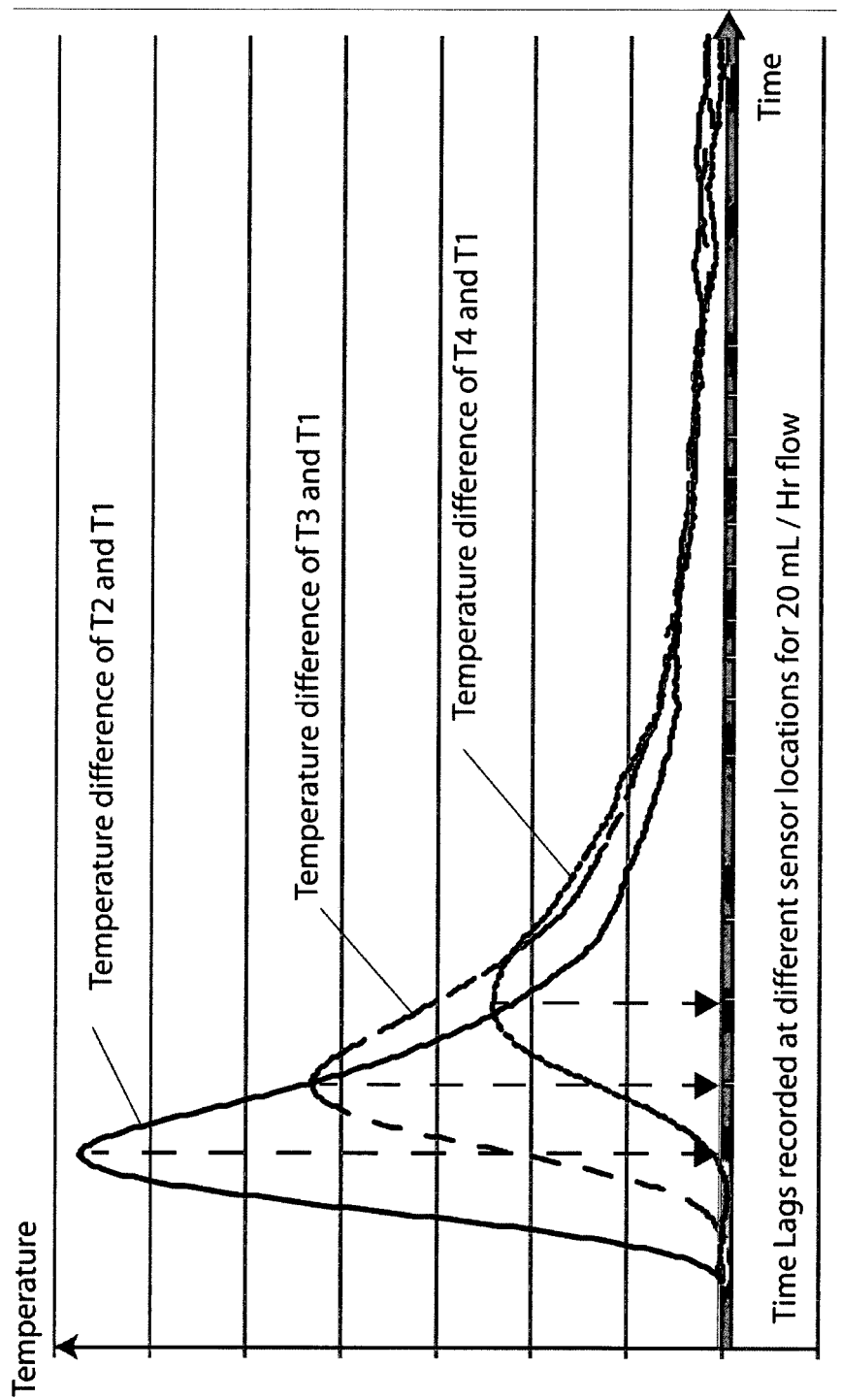
FIG. 6E is an example of temperature vs. time graphs of temperature difference measured with the Flow Cell and Flow Detection Unit shown in FIG. 2B.
Figure 10A:
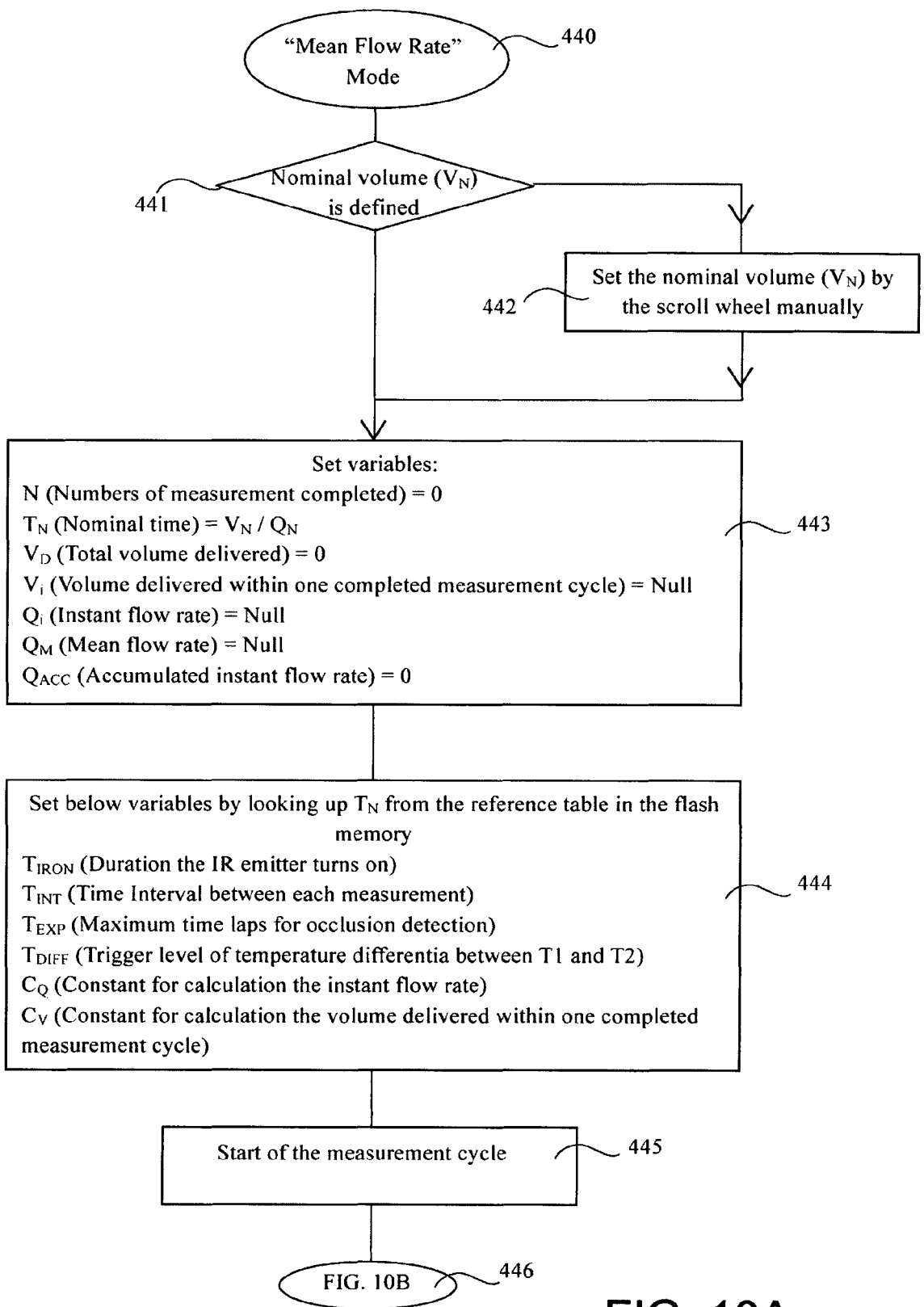
FIGS. 10A to 10C are flow diagrams illustrating the mean flow rate mode in accordance with an embodiment of the invention.

Referring to FIG. 10A, the Flow Detection Unit 100 is programmed to display mean flow rate (Q.sub.M) (step 440). Next, at step 441, the nominal volume (V.sub.N) is defined either by reading the barcode 212 or alternatively barcode 312 at step 412 (FIG. 8) or manually input by the user at step 442. Furthermore, manual input allows user to set the nominal volume (V.sub.N) in case of an invalid reading of the barcode 212 by the barcode reading means 112. The MCU 130 then sets the variables at step 443, which comprises the number of completed measurements (N), nominal time (T.sub.N), total volume delivered (V.sub.D), volume delivered within one completed measurement cycle (Vi), instant flow rate (Qi), mean flow rate (Q.sub.M) and the accumulated instant flow rate (Q.sub.ACC). Subsequently, the MCU 130 sets the measurement variables T.sub.IRON, T.sub.INT, T.sub.EXP, T.sub.DIFF, C.sub.Q, and C.sub.V (constant value for calculating the volume delivered within one completed measurement cycle), which are retrieved by looking up T.sub.N from a reference table stored in the Flash Memory of the Flow Detection Unit 100 (step 444). The algorithm developed is clearly not restricted to the use of the measurement of variables described above. The presence of more sensors and their locations relative to the heat source or sources will allow other permutations in the development of the algorithm for flow rate detection. For example, the determination of flow rates could be realized by comparing the variables or its derivatives or combinations of such resulting from a specific fluid flow with predetermined values established for known flow rates in a table. Referring to FIG. 6E, a 20 mL/hour fluid flow would manifest varying T.sub.Lap as well as temperature amplitudes, when measured at different sensor locations in a flow cell using four thermal sensors which, generate four temperature readings T1, T2, T3 and T4. These recordings could form inputs for developing an algorithm. For example, in situations where the flow rate is relatively fast, e.g. 100 mL/Hour, or relatively slow, e.g. 1 mL/Hour, it is possible that the temperature of the location at which one of the sensors is disposed is too close to or too far from the thermal source, and temperature measurements at this location may not be able to detect a clear signal. Embodiments with more sensors disposed at different locations along the fluid channel, provide solutions to enable temperature measurements at multiple locations. Shown in FIG. 6E as an example, multi-location measurement of temperature generates temperature difference comparison curves with respect to a reference location. This provides data to the Flow Detection Unit to record temperature measurements with meaningful readings for the purpose of flow rate detection and monitoring.

Figure 10B:
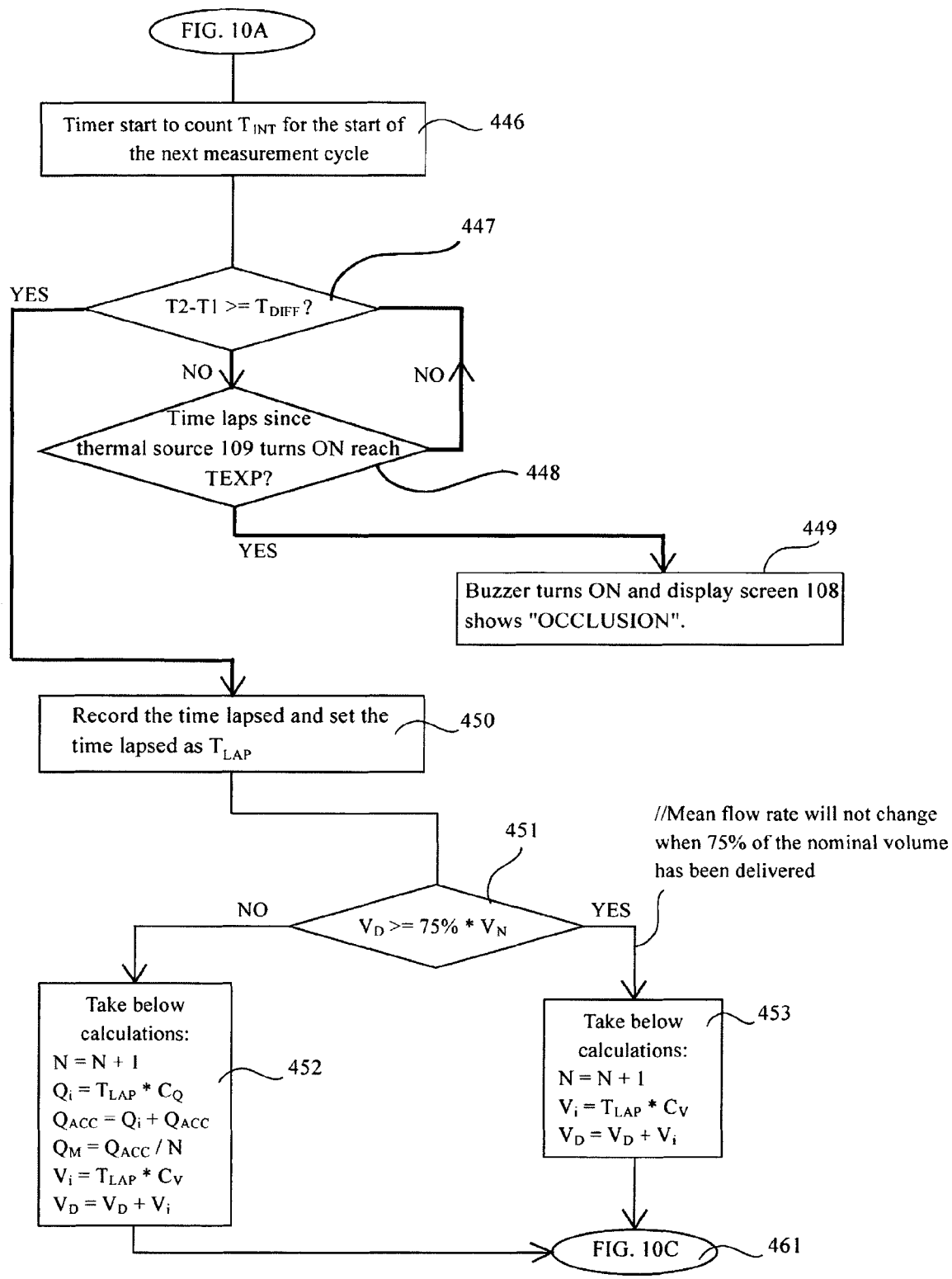
Figure 10C:
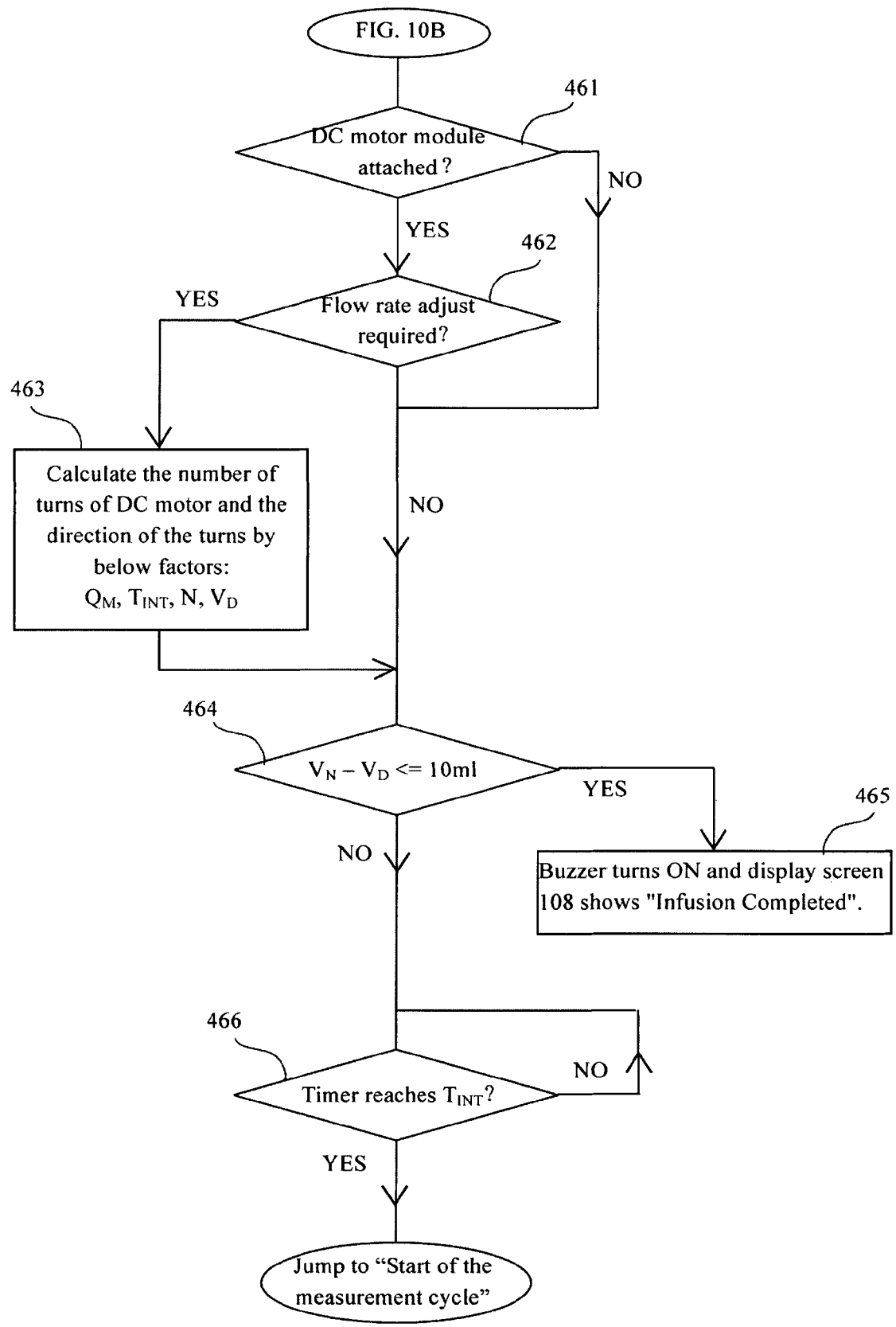

Referring back to FIG. 10A, at step 445, the thermal source 109 will be turned ON and OFF intermittently at the start of the measurement cycle. The subsequent steps 446-450 shown in FIG. 10B are similar to steps 424-427 of FIGS. 9A and 431 of FIG. 9B, and thus will not be described.

Next, at step 451, the volume delivered (V.sub.D) is compared against 75% of the nominal volume (V.sub.N). The mean flow rate (Q.sub.M) is the arithmetic mean of the all instantaneous flow rate (Qi) readings obtained as described above if the volume delivered (V.sub.D) is less than 75% of the nominal volume (V.sub.N) (step 452). The total volume delivered (V.sub.D) since the start of the first measured is also calculated. By definition, the mean flow rate (Q.sub.M) shown will change when each subsequent reading of instantaneous flow rate (Qi) changes.

When the volume delivered (V.sub.D) exceeds 75% of the nominal volume (V.sub.N) (step 453), the mean flow rate (Q.sub.M) displayed will be the cumulative volume over time. The cumulative volume is the sum of each unit of volume that is derived from the instantaneous flow rate (Qi) and the time interval (T.sub.INT) between each of these readings. The result of this is that the mean flow rate (Q.sub.M) displayed will approach a value that eventually represents the volume delivered (V.sub.D) over time. The total volume delivered (V.sub.D) since the start of the first measured is also calculated. One of the considerations in selecting a 75% threshold volume is that it corresponds to definition of mean flow rate in the International Organization for Standardization ISO 28620. By definition, averages of instantaneous flow rate (Qi) during the initial 75% of volume delivered (V.sub.D) will show more fluctuations in the readings. It can be appreciated that other threshold volume levels, such as 70% or 80% may be applicable.

At step 461, the MCU 130 checks if a DC motor module is attached to the flow rate regulating mechanism 230. If the DC motor module is available, the MCU checks whether any flow rate adjustment is required (step 462) based on Q.sub.M, T.sub.INT, N, and V.sub.D and calculates the number of turns and direction of turns for the DC motor (step 463) to, for example, adjust the axle 231 of the flow rate regulating mechanism 230.

If no DC motor module is available, the MCU 130 proceeds to determine whether the infusion is complete. For example, at step 464, the difference between the nominal volume (V.sub.N) and volume delivered (V.sub.D) is compared with a threshold level of, for example, 10 ml. If the difference of V.sub.N and V.sub.D is less than 10 ml, the buzzer is turned on and the display screen 108 indicates "Infusion Completed" (step 465). The remaining volume of medication fluid can be considered as residue volume. On the other hand, if the difference is more than 10 ml, the timer checks whether the measurement has reached the selected time interval T.sub.INT (step 466), which helps to control the measurement interval. If the interval has reach T.sub.INT, the measurement cycle restarts at step 445 in FIG. 10A.

It can be appreciated that the algorithm used may differ according to specific needs as it also relates to the performance characteristics of the fluid pump to which the device is attached and as such does not limit the scope of the invention. Furthermore, several embodiments of the invention have thus been described. However, those ordinarily skilled in the art will recognize that the invention is not limited to the embodiments described, but can be practiced with modification and alteration within the spirit and scope of the appended claims that follow.

The invention claimed is:

1. A device for measuring flow rate of a fluid passing through a fluid channel, the device comprising:
    a housing having a coupling interface to which the fluid channel is attachable;
    a thermal source disposed in the housing and adjacent to the coupling interface at a first location, wherein the thermal source is to emit a first thermal signal from the coupling interface into the fluid channel;
    a first thermal sensor disposed in the housing and adjacent to the coupling interface at a second location spaced apart from the first location with a first interval; wherein the first thermal sensor is to receive a first thermal signal at the coupling interface from the fluid channel;
    a microprocessor disposed in the housing and coupled to the thermal source and the first thermal sensor, wherein the microprocessor is to record a first instant at which the first thermal signal is emitted from the thermal source, a second instant at which a second thermal signal is received by the thermal sensor, and to determine the flow rate based on said first interval, the first instant, the first thermal signal, the second instant and the second thermal signal
    characterized in that
    the fluid channel includes a tubular member;
    the device includes a first plate and a second plate connected to each other with the tubular member sandwiched therebetween;
    wherein the tubular member being resiliently deformable, a distance between the first plate and the second plate is less than an external diameter of the tubular member such that the tubular member is compressed between the first plate and the second plate.

2. The device of claim 1, wherein the coupling interface includes a first end and a second end, the thermal source is positioned between the first end and the second end of the coupling interface.

3. The device of claim 2, wherein the first thermal sensor is positioned between the thermal source and the second end of the coupling interface.

4. The device of claim 3, further comprising a second thermal sensor disposed in the housing and adjacent to the coupling interface at a third location spaced apart from the first location with a second interval; wherein the second thermal sensor is coupled to the microprocessor and to receive a second thermal signal at the coupling interface from the fluid channel.

5. The device of claim 1, wherein the coupling interface is a slot having a first side surface and a second side surface opposite to each other for receiving the fluid channel therebetween.

6. The device of claim 5, wherein the thermal source and the first thermal sensor are positioned at the first side surface.

7. The device of claim 5, wherein the thermal source is positioned at the first side surface and the first thermal sensor is positioned at the second side surface.

8. A system for determining flow rate of an intravenous fluid delivery, the system comprising:
    a flow cell having a sidewall surrounding a fluid channel having an inlet and an outlet;
    a controller including:
        a housing to which the flow cell is attached;
        a thermal source disposed in the housing at a first position and adjacent to a first portion of the sidewall of the flow cell, wherein the thermal source is to emit a first thermal signal into the fluid channel;
        a first thermal sensor disposed in the housing at a second position and adjacent to a second portion of the sidewall of the flow cell, wherein the first thermal sensor is to receive a first thermal signal from the fluid channel;
        a microprocessor disposed in the housing and coupled to the thermal source and the first thermal sensor, wherein the microprocessor is to record a first instant at which the first thermal signal is emitted into the fluid channel, a second instant at which a second thermal signal is received from the fluid channel, and to determine the flow rate based on said first interval, the first instant, the first thermal signal, the second instant and the second thermal signal
    characterized in that
    the fluid channel includes a tubular member;
    the device includes a first plate and a second plate connected to each other with the tubular member sandwiched therebetween;
    wherein the sidewall being resiliently deformable, a distance between the first plate and the second plate is less than an external diameter of the tubular member such that the tubular member is compressed between the first plate and the second plate.

9. The system of claim 8, wherein the thermal source is positioned between the inlet and the outlet.

10. The system of claim 9, wherein the first thermal sensor is positioned between the thermal source and the outlet.

11. The system of claim 10, wherein the housing having a first side surface and a second side surface, the flow cell is disposed between the first side surface and the second side surface, wherein the thermal source is disposed on one of the first and second side surfaces and the first thermal sensor is disposed on said one of the first and second side surfaces.

12. The system of claim 10, wherein the housing having a first side surface and a second side surface, the flow cell is disposed between the first side surface and the second side surface, wherein the thermal source is disposed on one of the first and second side surfaces and the first thermal sensor is disposed on the other one of the first and second side surfaces.

13. The system of claim 10, further comprising a second thermal sensor disposed in the housing at a second position and adjacent to a third portion of the sidewall of the flow cell, wherein the second thermal sensor is coupled to the microprocessor and to receive a second thermal signal from the fluid channel.

14. The system of claim 13, wherein the second thermal sensor is positioned between the inlet and the thermal source.

15. The system of claim 14, wherein the housing having a first side surface and a second side surface, the flow cell is disposed between the first side surface and the second side surface, wherein the thermal source is disposed on one of the first and second side surfaces and the second thermal sensor is disposed on said one of the first and second side surfaces.

16. The system of claim 14, wherein the housing having a first side surface and a second side surface, the flow cell is disposed between the first side surface and the second side surface, wherein the thermal source is disposed on one of the first and second side surfaces and the second thermal sensor is disposed on the other one of the first and second side surfaces.

17. The system of claim 8, wherein the housing having a first plate and a second plate, the first plate and the second plate being movable relative to each other between a first position at which the flow cell is received between the first plate and the second plate, and a second position at which the flow cell is fixed between the first plate and the second plate.

18. The system of claim 17, wherein when the first plate and the second plate are at the second position, the fluid channel is compressed between the first plate and the second plate.

19. A method of detecting flow rate in an intravenous fluid delivery system, the method comprising:
   emitting a first thermal signal into a first location of a fluid delivery channel at a first instant, wherein the fluid delivery channel forms a segment of the intravenous infusion system;
   receiving a second thermal signal from a second location of the fluid delivery channel at a second instant, the second location is positioned with a first interval downstream from the first location;
   receiving a third thermal signal from a third location of the fluid delivery channel at a third instant, the third location is positioned with a second interval downstream from the second location;
   receiving a fourth thermal signal from a fourth location of the fluid delivery channel at a fourth instant, the fourth location is positioned with a third interval downstream from the third location;
   determining the flow rate by comparing the thermal signals from the second, third and fourth location of the delivery channel with predetermined temperature signal values established for known flow rates.

20. The method of claim 19, further comprising comparing a temperature difference between the second thermal signal and the third thermal signal with a trigger level to determine an occlusion situation.

21. The method of claim 19, wherein each thermal signal at the second, third and fourth location of the fluid channel includes a time taken for the fluid heated by the first thermal signal to pass through the respective first, second and third interval, the temperature amplitude at each of the second, third and fourth locations, the temperature differences between the second, third and fourth locations and the time taken for the temperature difference to reach a trigger level.

22. The method of claim 19, wherein each flow rate is determined by combinations of the predetermined thermal signal values established for known flow rates.

* * * * *